United States Patent [19]
Ikeda et al.

[11] Patent Number: 5,919,696
[45] Date of Patent: Jul. 6, 1999

[54] METHOD FOR MICROBIALLY DECOMPOSING ORGANIC COMPOUNDS AND METHOD FOR ISOLATING MICROORGANISM

[75] Inventors: Michio Ikeda, Fuchu; Takeshi Gotanda, Yokohama; Yuko Imamura, Tokyo; Chikako Hirakawa, Kobe, all of Japan

[73] Assignee: Kabushiki Kaisha Toshiba, Kawasaki, Japan

[21] Appl. No.: 08/749,355

[22] Filed: Nov. 20, 1996

[30] Foreign Application Priority Data

Nov. 20, 1995 [JP] Japan .................................. 7-301200

[51] Int. Cl.$^6$ .................. B09B 3/00; C12N 1/20; C12S 13/00
[52] U.S. Cl. ........................... 435/262.5; 435/30; 435/34
[58] Field of Search .............................. 435/30, 34, 262.5

[56] References Cited

U.S. PATENT DOCUMENTS

| | | | |
|---|---|---|---|
| 4,452,894 | 6/1984 | Olsen et al. | 435/253 |
| 5,316,940 | 5/1994 | Georgiou et al. | 435/252.1 |
| 5,455,173 | 10/1995 | Crawford et al. | 435/264 |
| 5,478,743 | 12/1995 | Perkins et al. | 435/262.5 |
| 5,543,317 | 8/1996 | Shields et al. | 435/240.2 |
| 5,571,705 | 11/1996 | Pierce | 435/174 |

FOREIGN PATENT DOCUMENTS

| | | |
|---|---|---|
| 2-92274 | 4/1990 | Japan . |
| 6-296711 | 10/1994 | Japan . |
| 7-96289 | 4/1995 | Japan . |
| 8-66182 | 3/1996 | Japan . |
| 8-228767 | 9/1996 | Japan . |
| 94/22605 | 10/1994 | WIPO . |
| 95/11766 | 5/1995 | WIPO . |

OTHER PUBLICATIONS

Schneider et al., Appl. Environ. Microbiol. 62(1), 13–19, 1996.
Haggblom et al., Appl. Environ. Microbiol. 54(12), 3043–3052, 1988.
Grosser et al., Appl. Environ. Microbiol. 57(12), 3462–3469, 1991.
Kleespies et al., Int. J. Syst. Bacteriol. 46(3), 683–687, 1996.

*Primary Examiner*—Kenneth R. Horlick
*Attorney, Agent, or Firm*—Finnegan, Henderson, Farabow, Garrett & Dunner, L.L.P.

[57] ABSTRACT

The method of isolating organic compound-degradable microorganisms included in this invention is characteristic in that microorganisms in the organic compound contaminated sample, for example an environment sample, are cultured in a carbon-free medium, at the same time, are contacted with organic compounds mainly as the gas phase, and selected by the tolerance to the organic compounds as the index. Also, the method for biodegradation of organic compounds is characteristic in that the microorganism thus isolated, for example, *Komagatella brevis*, is contacted with contaminated soil or contaminated underground water, and without the addition of additives or inducing substances for organic compounds decomposing enzymes, may effectively biodegrade the organic compounds in the environment.

30 Claims, 19 Drawing Sheets

METHOD FOR MICROBIALLY DECOMPOSING ORGANIC COMPOUNDS AND METHOD FOR ISOLATING MICROORGANISM

BACKGROUND OF THE INVENTION

1. Field of the Invention

The invention relates to a method for decomposing organic compounds by a microorganism having an organic compound decomposing ability, a apparatus for decomposing organic compounds by a microorganism having an organic compound decomposing ability, a method for isolating a microorganism, and a new organic compounds-degradable microorganism.

2. Description of the Related Art

Leakage into the environment of organic compounds including halogenated hydrocarbon such as trichloroethylene, dichloroethylene, vinyl fluoride, vinyl bromide, 3,3,3-trifluoro-2-propene and 2,3-dichlorohexafluoro-2-butene, and aromatic hydrocarbon such as toluene, phenol, bromobenzen, 1-bromonaphthalene and cresol used as a cleaning agent in various types of plants has become a serious problem in these years. As to the use of organic compounds, studies are now being made toward the restriction of their use. But, the environments which have been contaminated by organic compounds, for example, contaminated soil and contaminated underground water, are problems remained to be solved.

Under such circumstances, studies are being made on the cleaning of the environments such as soil and underground water contaminated by organic compounds. For example, proposals have been made to clean the contaminated environments by physical methods such as soil vapor-extracting and incinerating. As a technique which is inexpensive and has a lower environmental impact as compared with the physical methods, a method for decomposing organic compounds contaminated the environments by a microorganism is attracting attention. And, as techniques for directly treating organic compounds, a thermal or optical decomposing method are known. But, a method for decomposing an organic compound by a microorganism is attracting attention because this method is superior to the above treating techniques in costs and operability.

As examples of a method for decomposing an organic compound by a microorganism, the proposed are a method of using methanotroph which needs the addition of methane (see Japanese Patent Laid-Open Publication No. Hei 2-92274), and a method of using bacteria which needs the induction by an aromatic compound such as phenol, toluene or cresol (see Japanese Patent Laid-Open Publication No. Hei 8-66182), and a method of using mutagenized bacteria (see Japanese Patent Laid-Open Publication No. Hei 8-228767).

However, such conventional methods for decomposing an organic compound by a microorganism have disadvantages that it is hard to keep the decomposition efficiency (treating efficiency) of the organic compound because they need additives, inducers and mutagenized bacteria, and in the case of applying such methods to the clean up of contaminated environments, additional contamination (secondary contamination) may be caused because new substances including additives and inducers are added to the environment, resulting in not cleaning up the environment. Especially, the latter method is highly possible to additionally contaminating the environment because it uses a microorganism which needs the induction of the enzyme by an aromatic compound such as phenol, toluene or cresol which is hazardous to the environment. Furthermore, when mutagenized bacteria are scattered to the environment, it is a great menace to the safety in society.

In other words, the conventional methods for decomposing an organic compound by a microorganism have disadvantages that inducing substances must be added to the environment to induce enzymes necessary for decomposition, or mutagenized bacteria must be scattered to the environment for decomposition, and when inducers such as hazardous chemicals are necessary, or mutagenized bacteria are scattered to the environment, it is highly possible to cause secondary contamination if such conventional methods are applied to the cleanup of the contaminated environment, so that it is hard to clean the environment contaminated by an organic compound. And, the methods for decomposing an organic compound by a microorganism also have a disadvantage that it is hard to keep the decomposing operation and the decomposition efficiency because the additives and inducers are required.

Therefore, it is highly demanded to provide a method for decomposing an organic compound by which, for example, an organic compound in the contaminated environment can be decomposed effectively without adding any new substance such as an additive and inducer or mutagenized bacteria, to environment, and the decomposing operation and the decomposition efficiency of the organic compound can be kept easily; microorganisms which can effectively decompose organic compounds without requiring a new substance such as an additive or inducer; and a microorganism isolating method which can readily isolate the above microorganism.

SUMMARY OF THE INVENTION

The invention has been completed to remedy the above disadvantages and aims to provide a method for decomposing organic compounds which can effectively decompose organic compounds without requiring the addition of any additive or inducer, and if it is applied to the cleanup of, for example, contaminated environments, can lower environmental impact to the utmost; an apparatus for decomposing organic compounds using the method for decomposing organic compounds; a method for isolating a microorganism which can efficiently isolate a microorganism effective for biodegradation of organic compounds; and a new microorganism which can efficiently decompose organic compounds without requiring any additive or inducer.

The method for decomposing organic compounds according to the invention comprises the steps of contacting a microorganism, which is derived from the environment contaminated by a first organic compound or a sample contacted to said environment and has an organic compound decomposing ability, with said first and/or second organic compound, and decomposing said first and/or said second organic compound by said microorganism.

And, the method for decomposing organic compounds according to the invention comprises the steps collecting a microorganism from the environment contaminated by a first organic compound or a sample contacted to said environment, and culturing the collected microorganism so that its organic compound tolerance is used as an index, and selecting said cultured microorganism, and reselecting said selected microorganism with the organic compound decomposing ability as an index, and contacting said reselected microorganism to said first and/or second organic compound, and decomposing said first and/or said second organic compound by said microorganism.

And, the method for decomposing organic compounds according to the invention comprises the steps of collecting a microorganism from the environment contaminated by a first organic compound or a sample contacted to said environment, and culturing said collected microorganism under the same existing conditions of said first organic compound as those of said environment or said sample contacted to said environment, and selecting said cultured microorganism, and reselecting said selected microorganism with the organic compound decomposing ability as an index, and contacting said reselected microorganism to said first and/or second organic compound, and decomposing said first and/or said second organic compound by said microorganism.

The apparatus for decomposing organic compounds according to the invention comprises means for retaining a microorganism which is derived from the environment contaminated by a first organic compound or a sample contacted to said environment and has an organic compound decomposing ability, and means for contacting the microorganism retained by said retaining means to said first and/or second organic compound.

And, the method for isolating a microorganism according to the invention comprises the steps of collecting a microorganism from the environment contaminated by organic compounds or a sample contacted to said environment, and culturing the collected microorganism so that its organic compound tolerance is used as an index, and selecting said cultured microorganism, and reselecting said selected microorganism with an organic compound decomposing ability as an index.

And, the method for isolating a microorganism according to the invention comprises the steps of collecting a microorganism from the environment contaminated by organic compounds or a sample contacted to said environment, and culturing the collected microorganism under the same existing condition of said organic compound, and selecting said cultured microorganism, and reselecting said selected microorganism with an organic compound decomposing ability as an index.

The new microorganism according to the invention is isolated and having an organic compound decomposing ability, characterized by belonging to Komagatella, Arthrobacter, Brevibacter, Clavibacter, Mycobacterium, Renibacterium or Terrabacter.

And, the new microorganism according to the invention is isolated and identified having all the identifying characteristics of a deposit number YMCT-001 (FERM BP-5282) deposited on Nov. 2, 1995 at the National Institute of Bioscience and Human-Technology, Agency of Industrial Science and Technology of Japan.

A first method for decomposing organic compounds according to the invention uses a microorganism which is derived from the contaminated environment and has an organic compound decomposing ability in order to decompose the organic compounds. And, a second method for decomposing organic compounds according to the invention isolates a microorganism having an organic compound decomposing ability from the environment contaminated by organic compounds or a sample contacted to the environment with an organic compound tolerance and an organic compound decomposing ability as an index, and uses the isolated microorganism in order to decompose the organic compounds.

Besides, a third method for decomposing organic compounds according to the invention sets the conditions for culturing microorganisms so that the existing conditions of organic compounds become precisely identical with those of organic compounds existing in the environment or the sample which has contacted to the environment, in order to select microorganisms. And, a microorganism having an organic compound decomposing ability is isolated from the selected microorganisms, and the isolated microorganism is used to decompose the organic compounds. The expression "existing conditions of organic compounds" used here is a general idea of simultaneously indicating every conditions such as organic compounds' types, amounts, existing ratios, existing forms (gas, liquid, solid) and the like. The microorganism used to decompose the organic compounds has an organic compound tolerance and can grow with the sole organic compounds as the sole carbon source, so that the organic compounds can be decomposed effectively without requiring any additive or inducer. Besides, it is easy to retain a system for decomposing the organic compounds and to stabilize the decomposition efficiency of the organic compounds. Furthermore, by an apparatus for decomposing organic compounds to which the first, second or third method for decomposing organic compounds is applied, the retention of the organic compound decomposing ability and the stabilization of the decomposing efficiency can be made readily. Therefore, when the method for decomposing the organic compounds according to the invention is applied to the cleanup of the contaminated environment, the impact on the environment is very low and secondary contamination is not caused because this method does not need any additives or inducers and the microorganism itself is derived from the contaminated environment.

The organic compound in the present invention is a general term for various kinds of organic compounds which are represented by halogenated hydrocarbon such as trichloroethylene, cis-dichloroethylene, transdichloroethylene, 1,1-dichloroethylene, tetrachloroethylene, dichloroethane, trichloroethane, tetrachloroethane, vinyl chloride, carbon tetrachloride, vinyl fluoride, vinyl bromide, 3,3,3-trifluoro-2-propene and 2,3-dichlorohexafluoro-2-propene, and aromatic hydrocarbon such as toluene, phenol, cresol, dichlorobenzene, trichlorobenzene, bromobenzene, bromonaphthalene and polychlorobiphenyl. And, the microorganisms in the present invention are used as a general idea to include various kinds of bacteria, actinomycetes, mold, yeasts, myxomycetes, Algae, and protozoans.

And, the microorganisms such as bacteria, which are used to decompose the organic compound and derived from the contaminated environment, have an organic compound tolerance and generally can form colonies in the contaminated environment. And, it is highly possible that the organic compounds which are present in the vaporized form are directly contacted to the colonies in the atmosphere (gas phase). In this case, the microorganisms which are used to decompose the organic compounds and are derived from the contaminated environment are preferably microorganisms which can directly take the organic compounds from the atmosphere (gas phase) to use them as the carbon source so that they can biologically decompose the organic compounds included in liquids and also in the vaporized form in the atmosphere. Among the microorganisms having the above-described properties which are assumed to exist in many kinds, when bacteria belonging to, for example, Komagatella, Arthrobacter, Brevibacter, Clavibacter, Mycobacterium, Renibacterium or Terrabacter, are used in the method and apparatus for decomposing organic compounds according to the invention, these bacteria can directly take the evaporated organic compounds from the atmosphere (gas phase) to use as the source of carbon, so that the organic compounds in the form evaporated into the atmosphere (gas phase) can be decomposed biologically. However, when a new microorganism belonging to Komagatella to be described afterward, especially *Komagatella brevis*, is used in the method and apparatus for decomposing organic compounds according to the invention, *Komagatella brevis* has a good ability of directly taking the evaporated organic compounds from the atmosphere (gas phase) to use as the source of carbon, so that the organic compounds in the evaporated form in the atmosphere (gas phase) can effectively be decomposed biologically.

And, in the first and second method for isolating a microorganism according to the invention, the microorganisms collected from the contaminated environment are cultured under conditions that a high concentration of organic compounds is present, where the organic compound tolerance is used as an index, so that microorganisms having a high organic compound tolerance can be selected efficiently. And, since a microorganism having an organic compound decomposing ability is selected from the microorganisms which have been selected with the only organic compound tolerance as an index, a microorganism excelling in an organic compound decomposing property and a maintaining property for the organic compound decomposing apparatus can be isolated efficiently. Since a physiological demand is generally different depending on species of microorganisms, various kinds of microorganisms can be isolated by suitably varying the component and form of the culture medium without limiting to a single culture medium and also by suitably setting the conditions such as a temperature. And, a microorganism having a particular property can be isolated easily by culturing the microorganism under a prescribed culture condition.

And, the first method for isolating a microorganism can easily select such a microorganism having particular properties by culturing microorganisms under arbitrarily determined culturing conditions. Besides, the second method for isolating a microorganism can securely select a microorganism having the organic compound tolerance by culturing microorganisms with the existing conditions of organic compounds controlled to be identical with the environment where the microorganisms have been collected, and can efficiently isolate a microorganism having the organic compound decomposing ability.

And, the apparatus for decomposing organic compounds according to the invention retains a microorganism which is isolated from the environment contaminated by a first organic compound or a sample collected from the contaminated environment and has a high organic compound tolerance and organic compound decomposing ability, and contacts the retained microorganism with the first or second organic compound, so that it is easy to keep the organic compound decomposing ability and to stabilize the decomposing efficiency. The first and second organic compounds may be those in various kinds described above.

The apparatus for decomposing organic compounds according to the invention is not limited to a particular decomposing apparatus, and may be an organic compound decomposing apparatus which employs a mode using bioribbon, a mode using bioreactor, a mode using biofilter, a mode using injection, or a mode using biocolumn.

The apparatus for decomposing organic compounds which employs the mode using bioribbon has a microorganism having the organic compound decomposing ability, particularly the new microorganism of the present invention, carried into the interior of a hydrophobic porous membrane, buries the hydrophobic porous membrane carrying the microorganism in the ground to introduce the organic compounds contained in soil into the hydrophobic porous membrane by utilizing as a drive force the adhesion of the organic compounds to the hydrophobic porous membrane or the evaporative power of the organic compounds, and decomposes the organic compounds by the microorganism within the hydrophobic porous membrane. In the apparatus for decomposing organic compounds which employs the mode using bioribbon, the hydrophobic porous membrane serves as retaining means for retaining the microorganism and contacting means for contacting the microorganism retained by the retaining means and the organic compounds.

As the hydrophobic porous membrane, it is preferable to use a porous substance which is treated to be given a hydrophobic property with teflon or the like, or a porous substance containing a hydrophobic material such as teflon or the like. And, by adjusting the hydrophobic property of the hydrophobic porous membrane, the evaporative power of underground water can be used efficiently as a drive force at the time of introducing the organic compounds into the hydrophobic porous membrane.

And, according to the apparatus for decomposing organic compounds which employs the mode using bioribbon, the organic compounds can be decomposed efficiently without emphatically requiring any maintenance or energy after burying the decomposing apparatus in the ground.

The term "ground" is used as a general idea of including every environments under the ground surface, such as soil, soil water, underground water and everything containing them.

And, the apparatus for decomposing organic compounds which employs the mode using bioreactor contacts the pumped underground water, vacuum-extracted gas or dug soil to the microorganism having the organic compound decomposing ability held within the bioreactor, particularly the new microorganism of the invention in order to decompose the organic compounds within the bioreactor. In the apparatus for decomposing organic compounds which employs the mode using bioreactor, means for retaining the microorganism is generally a reaction vessel which is isolated from exterior, and means for contacting the microorganism retained by the retaining means and the organic compounds is a pump or introduction tube for introducing the underground water, vacuum-extracted gas or dug soil into the bioreactor's reaction vessel.

To retain the microorganism in the reaction vessel which is isolated from exterior and to contact the microorganism to the organic compounds in the bioreactor, the environments in the reaction vessel, such as a pH value, a temperature and a dissolved oxygen concentration, are kept at an appropriate level according to the physiological demands by the microorganism retained in the reaction vessel, so that the organic compound decomposing efficiency by the microorganism is enhanced and the organic compound decomposing reaction by the microorganism can be retained for a long period. In other words, the environment within the bioreactor is desired to be kept in a condition that the organic compound decomposing reaction by the microorganism becomes the best. Since the condition that the organic compound decomposing reaction becomes the best is variable depending on the species of the microorganism, the environment in the bioreactor is changed according to the requirement by the species of the microorganism retained in the reaction vessel as required. Therefore, in the apparatus for decomposing organic compounds which employs the mode using bioreactor, even a microorganism which cannot keep the organic composition decomposing activity in the natural environment can be used to decompose the organic compounds. And, the pumped underground water, vacuum-extracted gas or dug soil is adjusted to such an amount that the organic compound decomposing activity becomes the highest within the reaction vessel, then introduced into the reaction vessel which retains the microorganism.

Furthermore, to retain the microorganism in the bioreactor's reaction vessel, it is possible to retain the microorganism in a free state by floating the microorganism in a culture solution, but it is preferable to carry the microorganism on an appropriate carrier. By carrying the microorganism on a carrier, the microorganism can be retained in a high density, and the organic compounds can be decomposed more efficiently. Such a carrier can be changed according to the species of the microorganism as required, but it is preferable to contain a porous substance which can carry the microorganism. Such a porous substance is desired to be able to form, for example, a microhabitat for the microorganism. The microhabitat is a vary small habitat for the microorganism in a pore space of several micrometers.

The porous substance can be have various forms such as particles or layers, and may be one member or two or more members of porous substances comprising an inorganic material of soil particles having a nodule structure such as ceramics, glass, calcium silicate, silica, alumina and Kanumatsuchi, and an organic material such as activated carbon, urethane foam, photosetting resin, anion exchange resin, cellulose, lignin, chitin and chitosan. Such a porous substance is desired to be inexpensive. Besides, it is desired to have a structure suitable to retain and grow the microorganism, preferably having pore spaces of several micrometers to tens micrometers for example. And carriers that contain and fix inside, for example, calcium alginate gel, agarose gel, or carrageenan gel may also be preferred. In addition, they could be used as a combined carrier of porous substrate and hydrophilic gel.

Furthermore, the apparatus for decomposing organic compounds which employs the mode using biofilter contacts the vacuum-extracted gas, the gas containing organic compounds or the like to the microorganism having the organic compound decomposing ability which is carried on the filter in a filter case, particularly the new microorganism of the present invention, to decompose the organic compounds within the filter case. In the apparatus for decomposing organic compounds which employs the mode using biofilter, means for retaining the microorganism is generally the filter case which is isolated from exterior, and means for contacting the microorganism retained by the retaining means and the organic compounds is a pump or introduction tube for introducing the vacuum-extracted gas into the filter within the filter case.

In the apparatus for decomposing organic compounds which employs the mode using biofilter, to retain the microorganism in the filter case which is isolated from exterior and to contact the microorganism to the organic compounds, the environments in the filter case, such as a temperature and a dissolved oxygen concentration, are kept at an optimum level according to the physiological requirements by the microorganism retained in the filter case, so that the organic compound decomposing efficiency by the microorganism is enhanced and the organic compound decomposing reaction by the microorganism can be retained for a long period. In other words, the environment within the filter case is desired to be kept in a condition that the organic compound decomposing reaction by the microorganism becomes the best. Since the condition that the organic compound decomposing reaction becomes the best is variable depending on the species of the microorganism, the environment in the filter case is changed according to the requirement by the species of the microorganism retained in the reaction vessel as required. Therefore, in the apparatus for decomposing organic compounds which employs the mode using biofilter, even a microorganism which cannot keep the organic composition decomposing activity in the natural environment can be used to decompose the organic compounds. And, the vacuum-extracted gas or the like is adjusted to such an amount that the organic compound decomposing activity becomes the highest within the filter case, then introduced into the filter case which retains the microorganism.

Besides, to retain the microorganism in the filter case, the microorganism is carried on an appropriate filter, and materials for the filter include filter paper, unwoven or woven various kinds of natural fiber or plastic fiber, and plastic foam. And, as the filter, the above-described various kinds of carriers can be used. The filter materials are selected from those which are not dissolved by the organic compounds.

By the apparatus for decomposing organic compounds which employs the mode using biofilter, the organic compounds contained in the extracted gas can be decomposed efficiently, and this apparatus is often used to decompose the organic compounds existing in an unsaturated area of soil.

And, the apparatus for decomposing organic compounds which employs the mode using injection gives the microorganism having the organic compound decomposing ability, particularly the new microorganism of the present invention, into soil, to decompose the organic compounds by the microorganism given into soil in the natural environment. In the apparatus for decomposing organic compounds which employs the mode using injection, means for retaining the microorganism is generally a culture tank which keeps the microorganism in the form to be given into the environment such as soil, and means for contacting the microorganism retained by the retaining means and the organic compounds is a transport pump or supply tube for giving the microorganism into the environment by the retaining means.

To use a method of directly contacting the microorganism with the organic compounds in the environment, it is preferable that the microorganism which is known to decompose the organic compounds present in the environment, e.g., the new microorganism according to the present invention, is previously cultured to reach an appropriate amount and the cultured microorganism is given into the environment such as soil. And, to give the microorganism into the environment, it is desired that in order to provide the living environment for the microorganism to make the activity of the microorganism active and to enhance the organic compound decomposing reaction velocity by the microorganism in the environment, a substance such as glucose or oxygen in an appropriate amount is given into the environment as required. The substance such as glucose is desired to be given in the form of a liquid solution rather than in the form of a solid into the environment, so that the microorganism can use it readily and a loss in time and energy in the stirring work can be minimized.

Furthermore, when the substance such as glucose or oxygen in an appropriate amount is to be given other than the microorganism into the environment, the microorganism, the substance such as glucose and oxygen may be given separately into the environment, but it is preferable to mix them in advance in order to put the microorganism in an optimum condition before giving into the environment and then give into the environment.

When the method of directly contacting the microorganism to the organic compounds in the environment is used, the microorganism is preferably carried on a carrier. By carrying the microorganism on the carrier, the microorganism can be retained in a high density and protected in the struggle for existence with other organisms, so that the organic compounds can be decomposed efficiently. Such a carrier can be changed according to the species of the microorganism as required, but it is generally a porous substance as described above. Such a porous substance is desired to be able to form the microhabitat. The microhabitat serves to protect the microorganism from the severe environment. For example, even when the external environment gets so dry that the living of the microorganism may be affected, the microhabitat has capillary water therein, so that the water supply to the microorganism can be retained. And the microorganism within the microhabitat is protected from being caught and eaten by protoza or the like in the environment such as soil. Therefore, by artificially forming the microhabitat by the carrier which contains the porous substance, the viability of the microorganism can be improved.

The porous substance is desired to be inexpensive. Besides, in view of its application by putting into the environment such as soil, it is desired not to deteriorate the dispersability or movability in the environment such as soil. For example, it is preferably in the form of particles having a particle diameter of one micrometer to ten millimeters. And, it is also desired to have a structure suitable to retain and grow the microorganism, preferably having pore spaces of hundred nanometer to hundred micrometer for example.

In addition, the apparatus for decomposing organic compounds which employs the mode using biocolumn charges the microorganism having the organic compound decomposing ability, particularly the new microorganism according to the invention, or a carrier carrying the microorganism into a cylinder which comprises a water permeable substance, and buries the cylinder into soil to contact the water permeated into the cylinder and the microorganism retained in the cylinder, thereby decomposing the organic compounds by the microorganism within the cylinder. In the apparatus for decomposing organic compounds which employs the mode using biocolumn, the cylinder serves as retaining means for retaining the microorganism and also contacting means for permeating underground water moving in soil into the cylinder.

As the water permeable substance which forms the cylinder, a metal having porous structure, a ceramic having porous structre or like can be used. And, by adjusting the permeability in the cylinder, the permeated water in an appropriate amount is contacted with the microorganism charged into the cylinder, and the organic compounds can be decomposed by the microorganism. As the carrier for carrying the microorganism, the above-described various kinds of carriers can be used.

The apparatus for decomposing organic compounds which employs the mode using biocolumn can be suitably used to decompose the organic compounds which are mainly contained in underground water. And, according to the apparatus for decomposing organic compounds which employs the mode using biocolumn, the organic compounds can be decomposed economically and efficiently without requiring any maintenance or energy after burying the decomposing apparatus in the ground.

The new microorganism having the organic compound decomposing ability according to the present invention is obtained by the above-described microorganism isolating method according to the invention and bacteria belonging to Komagatella, Arthrobacter, Brevibacter, Clavibacter, Mycobacterium, Renibacterium or Terrabacter which decomposes the organic compounds. The new microorganism according to the invention is a bacterium belonging to Komagatella which is obtained by the isolating method of the invention and can decomposes organic compounds, and taxonomically classified as *Komagatella brevis* as described afterward. The bacteria classified as *Komagatella* brevis include the strain YMCT-001 to be described in detail afterward, which is one of the bacteria classified as *Komagatella brevis*. And, the strain YMCT-001 is not the only bacterium classified as *Komagatella brevis*. In other words, the bacteria classified as *Komagatella brevis* are species containing strains other than the strain YMCT-001.

The bacteria belonging to Komagatella, Arthrobacter, Brevibacter, Clavibacter, Mycobacterium, Renibacterium or Terrabacter are isolated as the bacteria having the organic compound decomposing ability by selecting the microorganism with the tolerance against the organic compounds in a high concentration as the sole index, or selecting with the existing conditions for the organic compounds adjusted to be the same as the environment where the microorganism has been collected. And, it is possible to grow the organic compounds as the sole carbon source.

Among bacteria belonging to Komagatella, *Komagatella brevis* has a high ability to decompose various kinds of organic compounds represented by halogenated hydrocarbon such as trichloroethylene (hereinafter called "TCE"), cis-dichloroethylene (hereinafter called "cis-DCE"), trans-dichloroethylene (hereinafter called "trans-DCE), 1,1-dichloroethylene (hereinafter called "1,1-DCE), tetrachloroethylene, dichloroethane, trichloroethane, tetrachloroethane, vinyl chloride, carbon tetrachloride, vinyl fluoride, vinyl bromide, 3,3,3-trifluoro-2-propene and 2,3-dichlorohexafluoro-2-butene, and aromatic hydrocarbon such as toluene, phenol, cresol, dichlorobenzene, trichlorobenzene, bromobenzene, 1-bromonaphthalene and polychlorobiphenyl without requiring an additive or derivative substance. *Komagatella brevis* is tolerant to organic compounds when the concentration of organic compounds in its living environment is less than about 500 ppm, and grow by decomposing the surrounding organic compounds. Generally, to decompose hazardous substances such as organic compounds by microorganisms, the microorganisms are placed in an oligotrophic state so that they have to use the hazardous substances as carbon sources. The reason is that when there are substances, which can be easily used as carbon sources by the microorganisms, together with the hazardous substances, the substances which can be easily used as the carbon sources are used priorly over the hazardous substances by the microorganisms. However, even when a carbon source that *Komagatella* brevis can utilize, such as glucose, and organic compounds both exist in the environment, it decomposes not only glucose, but at the same time, decomposes organic compounds as well. In this case, even when the carbon source except for organic compounds, such as glucose exists in the living environment of *Komagatella brevis* in the range of less than 10000 mg/L with organic compounds, *Komagatella brevis* maintains its ability to decompose organic compounds. In addition, when glucose exists in the range of less than 1800 mg/L, they can still maintain the decomposing ability at the same or to a higher extent as when glucose does not exist. Therefore, *Komagatella brevis* excels in effectiveness and utility with respect to the cleanup of the contaminated environment, and is used in a very wide range. Moreover, the speed of decomposition of organic compound is in proportion of the number of *Komagatella brevis* bodies at the start of decomposition of organic compounds, so by adjusting the number of bacterial cells of *Komagatella brevis* which contact with organic compounds based in the concentration of organic compounds, the speed of decomposition of organic compounds can be controlled. Direct addition of *Komagatella brevis* into the sample containing the organic compounds is one of the methods to make *Komagatella brevis* and organic compounds into contact, but when *Komagatella brevis* is immobilized on various carriers and made into contact with organic compounds, it is made possible to make a large amount of bacterial bodies in contact with organic compounds thus the speed of decomposition of organic compounds could be made higher. The bacterium belonging to Komagatella according to the invention, particularly the strain YMCT-001 which is one of the bacteria classified as *Komagatella brevis*, has been deposited as "FERM BP-5282" in National Institute of Bioscience and Human-Technology, Agency of Industrial Science and Technology.

DESCRIPTION OF THE PREFERRED EMBODIMENTS

Preferred embodiments of the invention will be described below.

The method for decomposing organic compounds of the present invention basically uses a microorganism having a decomposing ability against organic compounds which is derived from the environment contaminated by organic compounds or a sample contacted to the contaminated environment. One embodiment of the method for decomposing organic compounds according to the invention will be described in detail with reference to FIG. 1.

Figure 1:
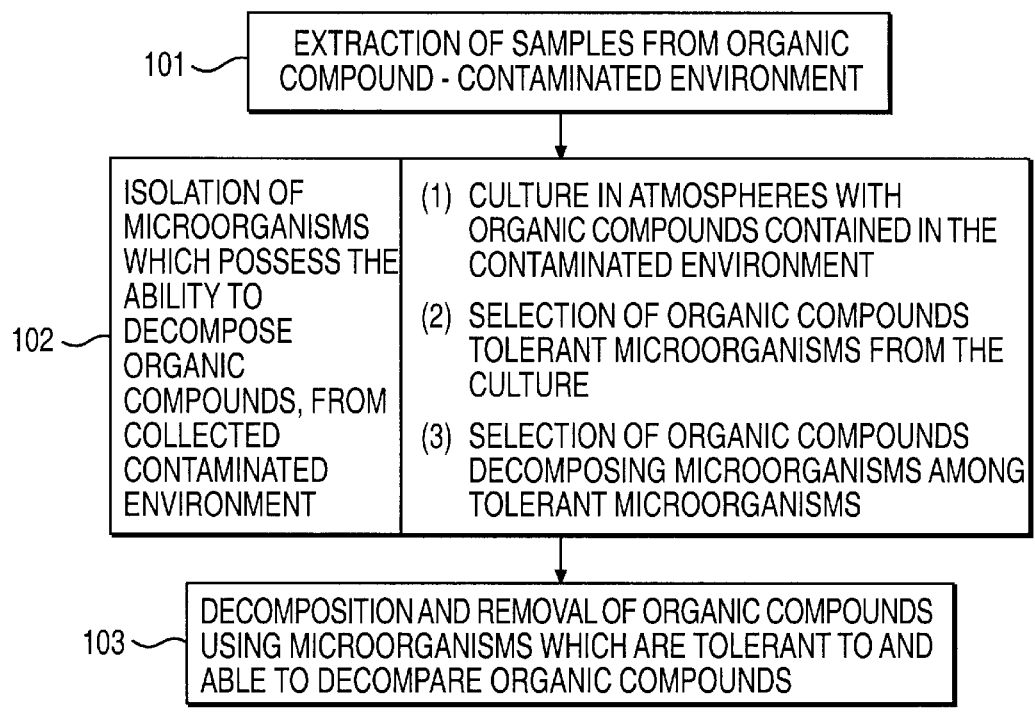
FIG. 1 is a diagram showing a processing example of the method for decomposing organic compounds according to the invention and an example of the method for isolating a microorganism according to the invention.

First, samples (contaminated environment) are taken from the environment contaminated by organic compounds (101 in FIG. 1). The contaminated environment from which the samples are collected is any environment contaminated by organic compounds and not particularly specified. For example, it may be contaminated soil, contaminated underground water, or contaminated river water. And, the organic compounds which are contaminants are TCE, cis-DCE, trans-DCE or 1,1-DCE and not particularly specified.

Then, microorganisms having organic compound decomposing ability are isolated from the collected contaminated environment or the samples contacted to the contaminated environment (102 in FIG. 1). Among the microorganisms which grow in the organic compounds present in the collected contaminated environment, a microorganism having the organic compound decomposing ability is selected. Thus, a microorganism which is tolerant against the organic compounds and can grow with the organic compounds as the carbon source can be isolated efficiently. In other words, a microorganism tolerance against organic compounds and having the organic compound decomposing ability can be isolated efficiently. The microorganism isolated as described above exerts a stable organic compound decomposing ability favorably without using any additive or inducer in the process of decomposing the organic compounds described afterward, so that the stable and efficient decomposition of the organic compounds can be retained readily.

The microorganism organic compound-degrading may be any kind which can be obtained in the above-described isolating process (to be described afterward in detail) and not limited to specific microorganisms. For example, they are bacteria belonging to Micrococcus, Stomatococcus, Planococcus, Staphyrococcus, Actinomyces, Amycolota, Arthrobacter, Brevibacterium, Clavibacter, Corynebacterium, Gordona, Komagatella, Mycobacterium, Nocardia, Pimelobacter, Renibacterium, Rhodococcus, and Terranacter. Table 1 shows typical bacteria of the above genera. As to the bacteria of the Micrococcus family, Japanese Patent Laid-Open Publication No. Hei 7-96289 discloses to use the bacteria of Micrococcus or Staphyrococcus, but it has been revealed that all species of the bacteria belonging to the above genera do not always exert a good organic compound decomposing ability under actual contaminated environments.

The environment which actually needs clean up generally has a pH value of 4 to 10 as a first condition, a temperature of 277 to 313K as a second condition in addition to the first condition, and an organic compound concentration of 30 ppb to 500 ppm as a third condition in addition to the first and second conditions. If microorganisms cannot live and increase in the above-described environment, cannot retain the organic compound decomposing ability for a long period, or cannot decompose organic compounds in a shorter period, they cannot be used to decompose organic compounds by being left in, contacted to, sprayed over contaminated soil or contaminated underground water, filled into a container and buried, or fixed onto a carrier and sprayed.

Among the microorganisms obtained through a cultured process and a process of selecting microorganisms which are tolerant against organic compounds in the method of isolating a microorganism of the present invention, the inventors have evaluated the organic compound decomposing activity (specifically, TCE decomposing ability) of bacteria in the above-described contaminated conditions. As a result, it was found that the bacteria usable to decompose organic compounds under the first and second conditions are species which are given symbols Δ, ○ and ⊚ on the organic compound decomposing ability as shown in Table 1. To satisfy up to the third condition, the species have to be given symbols ○ and ⊚. The species given the symbol ⊚ are most preferable because they can decompose organic compounds in a shorter period (90% or more is decomposed in five days). It is assumed that these bacteria have some oxidases (e.g., methane mono-oxygenase, toluene mono-oxygenase, ammonia oxidase or the like) within their body, or discharge such oxidases from the body, and such enzymes are related to the decomposition of organic compounds.

TABLE 1

| Genus | Species | TCE decomposing ability |
|---|---|---|
| Actinomyces | A. bovis | Δ |
| Amycolota | A. autotrophica | ○ |
| Arthrobacter | A. globiformis | ⊚ |
| Brevibacter | B. globiformis | ⊚ |
| Clavibacter | C. michiganensis | ⊚ |
| Corynebacterium | C. diphtheriae | Δ |
| Gordona | G. bronchialis | Δ |
| Komagatella | K. brevis | ⊚ |
| Micrococcus | M. agilis | ○ |
|  | M. halobius | ○ |
|  | M. kristinae | ○ |
|  | M. luteus | Δ(−) |
|  | M. lylae | ○ |
|  | M. nishinomiyaensis | ○ |
|  | M. roseus | ○ |
|  | M. sedentarius | ○ |
|  | M. varians | ○ |
| Mycobacterium | M. tuberculosis | ⊚ |
| Nocardia | N. asteroides | ○ |

TABLE 1-continued

| Genus | Species | TCE decomposing ability |
|---|---|---|
| Pimelobacter | P. simplex | ○ |
| Planococcus | P. citreus | ○ |
|  | P. kocurii | ○ |
| Renibacterium | R. sallmoninarum | ⊚ |
| Rhodococcus | R. rhodochrous | ○ |
| Staphylococcus | S. aristtae | ○ |
|  | S. aureus | Δ(−) |
|  | S. auricularis | ○ |
|  | S. capltis | ○ |
|  | S. caprae | ○ |
|  | S. carnosus | ○ |
|  | S. caseoticus | ○ |
|  | S. chromogenes | ○ |
|  | S. cohnii | Δ |
|  | S. delphini | ○ |
|  | S. epidermidis | ○ |
|  | S. equorum | ○ |
|  | S. felis | ○ |
|  | S. gallinarum | ○ |
|  | S. haemolyticus | Δ |
|  | S. hominis | ○ |
|  | S. hyicus | ○ |
|  | S. intermedius | ○ |
|  | S. kloosii | ○ |
|  | S. lentus | ○ |
|  | S. lugdunensis | x |
|  | S. saccharolyticus | ○ |
|  | S. saprophyticus | ○ |
|  | S. schleiferi | ○ |
|  | S. sciuri | ○ |
|  | S. simulans | Δ |
|  | S. warnneri | ○ |
|  | S. xylosus | ○ |
| Stomatococcus | S. mucilaginosus | ○ |
| Terrabacter | T. tumescens | ⊚ |

TCE decomposing ability (1 ppm, 5 days, 293K):
⊚ = not less than 90%,
○ = not less than 75%,
Δ = not less than 40%,
x = less than 10%, Now, description will be made in detail of a process of isolating microorganisms having the organic compound decomposing ability with the above-described bacteria as examples.

First, microorganisms collected from the contaminated environment are cultured with an appropriate amount of organic compound added (102-1 in FIG. 1). Microorganisms (tolerant bacteria) which are tolerant against a high concentration of organic compounds are selected from the culture (102-2 in FIG. 1). Furthermore, the existing condition of organic compound could be adjusted to as the same as in the environments where the bacteria was collected from. A selection example of the tolerant bacteria will be shown below. The inorganic salt culture medium used in the following case (including the embodiments to be described afterward) has the following components. The culture medium is changed according to the physiological demands by microorganisms to be extracted and not limited to the following inorganic salt culture medium. [Inorganic salt culture medium components (in 1 L of the inorganic salt culture medium)]

| | | |
|---|---|---|
| $Na_2HPO_4$ | 9.8 | g |
| $KH_2PO_4$ | 1.7 | g |
| $(NH_4)_2SO_4$ | 1.0 | g |
| $MgSO_4 \cdot 7H_2O$ | 0.1 | g |
| MgO | 10.75 | mg |

-continued

| | | |
|---|---|---|
| CaCO$_3$ | 2.0 | mg |
| ZnSO$_4$.7H$_2$O | 1.44 | mg |
| FeSO$_4$.7H$_2$O | 0.95 | mg |
| CoSO$_4$.7H$_2$O | 0.28 | mg |
| CuSO$_4$.5H$_2$O | 0.25 | mg |
| H$_3$BO$_3$ | 0.06 | mg |
| Strong hydrochloric acid | 51.3 | µL |

First, underground water or soil which is contaminated by, for example, a high concentration of TCE is collected. The underground water itself, or in the case of soil, its extract is inoculated on an inorganic salt agar culture medium, or is added to 0.1 mL of 0.1M phosphate buffer and 0.5 mL of top agar and layered on an inorganic salt agar culture medium made in a tightly sealable container. The extract is an aqueous solution prepared by placing 1 g of soil and 9 g of distilled water in a sterilized vial, mixing them therein, and treating by supersonic waves or thoroughly shaking. The top agar is layered and after it solidifies, a TCE-acetonitrile solution for example is added, and the container is tightly closed. The container is placed in a incubator adjusted to 298K, and cultivation is conducted for about five to ten days. At this time, the organic compound such as TCE is added to adjust the gaseous phase concentration of the organic compounds in the closed container to, for example, 50 to 10000 ppm. Then, a colony appearing on the agar medium or the top agar selected by a platinum loop to obtain organic compound tolerant bacteria.

Then, microorganisms (decomposing bacteria) having the organic compound decomposing ability are selected from the above-described organic compound tolerant bacteria (102-3 in FIG. 1). An example of selecting the decomposable bacteria will be described below.

Figure 2:
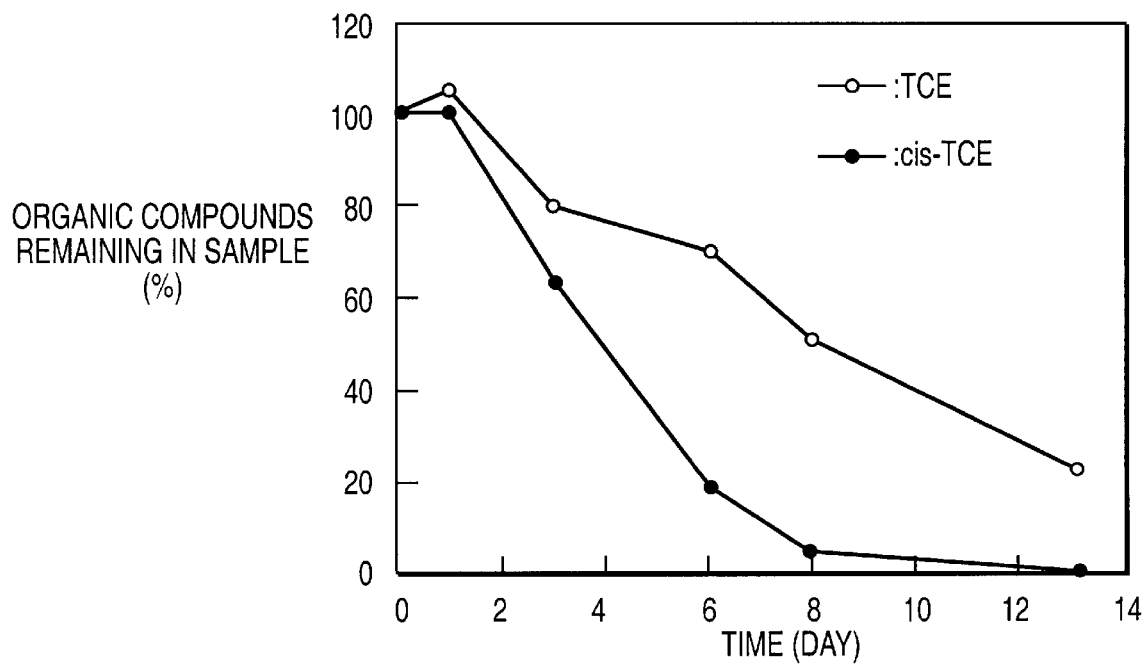
FIG. 2 is a diagram showing an example of the decomposition test results in the process of selecting a microorganism in the example of the method for isolating a microorganism shown in FIG. 1.

The selected tolerant bacteria are inoculated on LB liquid culture medium and pre-cultured by an overnight shaking cultivation under conditions of, for example, 298 k and 100 rpm to prepare bacterial suspensions. Then, bacterial cells from 100 µL of the bacterial suspension (OD$_{660}$=1) and 25 mL of an inorganic salt culture medium are placed in a vial, and organic compounds, e.g., TCE and cis-DCE are added in an amount of 1 ppm respectively. The vial is tightly closed by a teflon-coated butyl rubber cap and an aluminum cap seal, shaking culture is conducted under the conditions of 298K and 100 rpm, decomposition of the organic compounds is observed, and tolerant bacteria having the organic compound decomposing ability are selected. Thus, bacteria having the organic compound tolerance and the organic compound decomposing ability are obtained. The concentration of organic compounds is measured by a head space method using a gas chromatograph to calculate a decomposition rate of the organic compounds. FIG. 2 shows one example of the decomposition test result of the organic compounds by the tolerant bacteria.

Since the above-described process of isolating microorganisms having the organic compound decomposing ability cultures microorganisms, e.g., bacteria, in the contaminated environment in an atmosphere containing a high concentration of organic compounds at one point, the number of bacteria can be reduced, so that the organic compound tolerant bacteria can be selected efficiently. At this time, various kinds of organic compounds can be used as the organic compounds, but when the organic compounds present in the environment where the microorganisms were collected are used, microorganisms (e.g., bacteria) which are tolerant against the organic compounds can be selected easily. And, by culturing under the conditions that TCE or the like is added to adjust the gaseous phase concentration in a range of 50 to 10000 ppm, microorganisms which have higher tolerance and can be grown with the organic compounds such as TCE as the sole carbon source can be selected very efficiently. If the organic compounds such as TCE have a gaseous phase concentration of less than 50 ppm, the number of live bacteria after the culture increases, the efficiency of selecting the tolerant bacteria is lowered, and the obtained tolerant bacteria may have insufficient tolerance against the organic compounds. On the other hand, if the organic compounds such as TCE have a gaseous phase concentration of more than 10000 ppm, the efficiency of selecting the tolerant bacteria is lowered. And, the efficiency of isolating bacteria which have the organic compound decomposing ability is 1/38 of all colonies appeared when the organic compounds such as TCE have a gaseous phase concentration in a range of 50 to 100 ppm, 1/4 of all colonies appeared when they have a gaseous phase concentration in a range of 100 to 4000 ppm, 1/1 of all colonies appeared when they have a gaseous phase concentration in a range of 4000 to 8000 ppm, and 1/2 of all colonies appeared when they have a gaseous phase concentration in a range of 8000 to 10000 ppm, thus the bacteria having the organic compound decomposing ability can be isolated at a high ratio. Therefore, the gaseous phase concentration of the organic compounds such as TCE at culturing is more preferably in a range of 4000 to 8000 ppm.

And, in the process of isolating microorganisms having the organic compound decomposing ability, to culture the microorganisms collected from the contaminated environment under the conditions that the organic compounds are present in a high concentration, the microorganisms contained in the sample are inoculated in an appropriate amount on a solid culture medium by a platinum loop or the like and cultured under the condition that the gaseous phase concentration of the organic compounds is in a range of 50 to 10000 ppm, and the microorganism colonies and the organic compounds are directly contacted in the atmosphere (gas phase) because the microorganisms tolerance against the organic compounds often form colonies on the solid culture medium. By contacting the microorganism colonies with the organic compounds having a gaseous phase concentration in a range of 50 to 10000 ppm in the atmosphere (gas phase), the microorganisms possibly having the organic compound decomposing ability can be selected efficiently and readily, so that the pure culture of microorganisms can be readily made from the selected colonies as required. Therefore, the microorganisms having the organic compound decomposing ability can be isolated quickly and surely. When the microorganisms collected from the contaminated environment are cultured under the condition that the organic compounds are present at a high concentration, the culture medium components such as a pH value and the culture temperature can be changed as required, and properties required for the microorganisms, e.g., the culture medium components such as a pH value and the culture temperature, are changed as required according to the growing conditions, so that microorganisms having desired properties (e.g., growing conditions) can be isolated easily. And, as the culture medium for culturing microorganisms, it is desired to use a culture medium, e.g., a solid culture medium or the like, where microorganisms can form colonies.

And, by selecting the microorganisms (e.g., the above-described decomposing bacteria) having the organic compound decomposing ability from the microorganisms (e.g., the above-described tolerant bacteria) selected with the only organic compound tolerance as an index, the microorganisms which can be grown with the organic compounds as the sole carbon source and have a high organic compound decomposing ability can be isolated efficiently. In other words, the microorganisms which decompose the organic compounds without requiring any additive or inducer and have a good stability in the organic compound decomposing process can be obtained efficiently. And, to select the microorganisms for decomposing the organic compounds from the microorganisms tolerance against the organic compounds, the selecting process is performed by using various kinds of organic compounds according to the application, so that the microorganisms, e.g., bacteria, having the decomposing ability for various kinds of organic compounds can be obtained easily. The microorganism may be one which has the decomposing ability against a single kind of organic compound depending on the application, but the microorganism having the decomposing ability against various kinds of organic compounds is highly desired in practical viewpoint when it is used for clean up of the environment.

The above-described process is equivalent to the method for isolating microorganisms of the present invention. And, the new microorganism of the invention, YMCT-001 (deposited as "FERM BP-5282" in National Institute of Bioscience and Human-Technology, Agency of Industrial Science and Technology) which is one of the bacteria classified as *Komagatella brevis*, having the chlorinated organic composition decomposing ability, is one of the microorganisms obtained by the microorganism extracting process based on the selecting example of microorganisms tolerance against the above-described organic compounds and the selecting example of microorganisms which decompose organic compounds described above. The YMCT-001 will be described in detail afterward.

Then, the microorganisms, e.g., bacteria, which are obtained in the isolating process of the microorganisms having the organic compound decomposing ability, are tolerant against the organic compounds and have the organic compound decomposing ability, are contacted with the organic compounds to be decomposed in order to effect biodegradation of the organic compounds (103 in FIG. 1). This biodegradation process can be applied to a biodegradation treatment of various kinds of organic compounds, such as decomposition of organic compounds (including wastewater or waste gas containing organic compounds) as wastes or cleanup of the environment contaminated by organic compounds.

The above-described biodegradation process of organic compounds can biologically decompose organic compounds effectively without requiring any additive or inducer, and uses microorganisms (e.g., bacteria) which are isolated from the contaminated environment, so that it is free from causing secondary contamination due to an additive or inducer hazardous to the environment, or due to spraying of microorganisms. Besides, since no additive or inducer is required, the biodegradation of organic compounds can be retained easily. Therefore, this process is particularly effective for the cleanup of the contaminated environment. For example, when organic compounds are biologically decomposed as part of the environment cleanup, the organic compounds to be decomposed can be decomposed by contacting with the microorganisms (e.g., bacteria) in the contaminated environment containing the organic compounds, and the contaminated environment can be cleaned effectively with environmental impact lowered as low as possible. The contaminated environment to be cleaned includes soil, underground water and river water as described above.

The organic compounds to be subjected to the biodegradation include TCE, cis-DCE, trans-DCE, 1,1-DCE, tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichlorohexafluoro-2-butene, dichlorobenzene, bromobenzene, 1-bromonaphthalene and polychlorinated biphenyl as described above, and the decomposing bacteria can be suitably selected depending on the organic compounds to be subjected to the biodegradation. In particular, YMCT-001 according to the invention has the decomposing ability against any one of the above-described organic compounds and can be used broadly, excelling in practical use.

Now, description will be made of the bacterium belonging to Komagatella which is one of the microorganisms obtained by the above-described isolation of the microorganisms having the tolerance against the organic compounds and the microorganism isolation process based on the selection of the microorganisms for decomposing the organic compounds, particularly the strain (hereinafter called "strain YMCT-001") representing *Komagatella brevis*, namely one of the new microorganisms according to the present invention.

The strain YMCT-001 has the following bacteriological properties.

(a) Morphological properties etc.
  (1) Cell shape and size
    Nutrient agar culture medium:
      Short rods (0.9 to 1.1 by 1.5 to 1.8 $\mu$m) are formed when cultured at 30° C. for 6 hours
      Coccoid short rods (1.0 to 1.2 by 1.2 to 1.3 $\mu$m) when cultured at 30° C. for 24 hours
    Nutrient broth culture medium:
      No growth observed when cultured at 30° C. for 6 hours
      Coccoid short rods (1.0 to 1.2 by 1.1 to 1.3 $\mu$m) when cultured at 30° C. for 24 hours
  (2) Polymorphism: Observed : Rod-coccus cycle observed (However, not clearly)
  (3) Motility: –
  (4) Spore: –
  (5) E-longation of cell border colony: –
(b) Cultural properties
  (1) Nutrient agar plate culture: Colonies are smooth, wavy edges and slight glossy. : Pigments or diffusible pigments are not produced.
  (2) Nutrient broth culture: Growth of whole culture medium and a small amount of precipitation observed, formation of surface film not observed
  (3) Nutrient gelatin stab culture: Growth on the upper part observed, liquefaction not observed
  (4) Litmus milk: Growth not observed
(c) Physiological properties
  (1) Gram stainability: +
  (2) Nitrate reduction: +
  (3) Nitrite reduction: –
  (4) Denitrification reaction: –
  (5) MR test: –
  (6) VP test: –
  (7) Indol test: –
  (8) Hydrogen sulfide production TSI agar: –
    Lead acetate liquid culture medium: –
  (9) Starch hydrolysis: –
  (10) Utilization of citric acid Koser culture's medium:
    Slight Christensen's culture medium: +

(11) Utilization of inorganic nitrogen source Nitrate: −Ammonium salt: +

(12) Pigments formation: −

(13) Ureaze: −

(14) Oxidase: −

(15) Catalase: +

(16) Range for growth pH: 6.0 to 8.5 (optimum 7.0 to 8.5) Temperature: 4 to 39° C. (optimum 20 to 27° C.)

(17) Aerobic growth: +

(18) O-F test: −

(19) Acid from
L-arabinose: D-xylose: −
D-glucose: −
D-mannose: −
D-fructose: −
D-galactose: −
Maltose: −
Sucrose: −
Lactose: −
Trehalose: −
D-sorbitol: −
D-mannitol: −
Inositol: −
Glycerin: −
Starch: −
Raffinose: −
Saccharose: −
Cellobiose: −
Mannite: −

(20) Gas from
L-arabinose: −
D-xylose: −
D-glucose: −
D-mannose: −
D-fructose: −
D-galactose: −
Maltose: −
Sucrose: −
Lactose: −
Trehalose: −
D-sorbitol: −
D-mannitol: −
Inositol: −
Glycerin: −
Starch: −

(d) Other physiological properties (1) Arginine hydrolysis: −

(2) Esculin Hydrolysis: −

(3) Tween80 hydrolysis: +

(4) DNase: −

(5) Gelatin hydrolysis: −

(6) Acid-fast: −

(e) Chemical taxonomical properties (1) G+C of the DNA: 72 (mol %)

(2) Diamino acid of cell wall: meso-diaminopimelic acid (3) Arabinogalactan polymer of cell wall: −

(4) Glycolyl test: −

(5) Kind of cell lipid
Mycolic acid: −
Quinone based: MK-8 ($H_4$)

In view of the above-described bacteriological properties, and by further search according to "Bergey's Manual of Systematic Bacteriology, Volume 2, 1986" and "Bergey's Manual of Determinative Bacteriology, 1994". Strain YMCT-001 was identified as Corynebacterium which does not form spores, is a gram-positive bacillus exposing polymorphism in cell shape, and exists widely in the natural environment, for example in the soil. However, strain YMCT-001 was differs in its properties from any other strains mentioned in the above references, thus the taxonomical position of strain YMCT-001 could not be determined.

Figure 3:
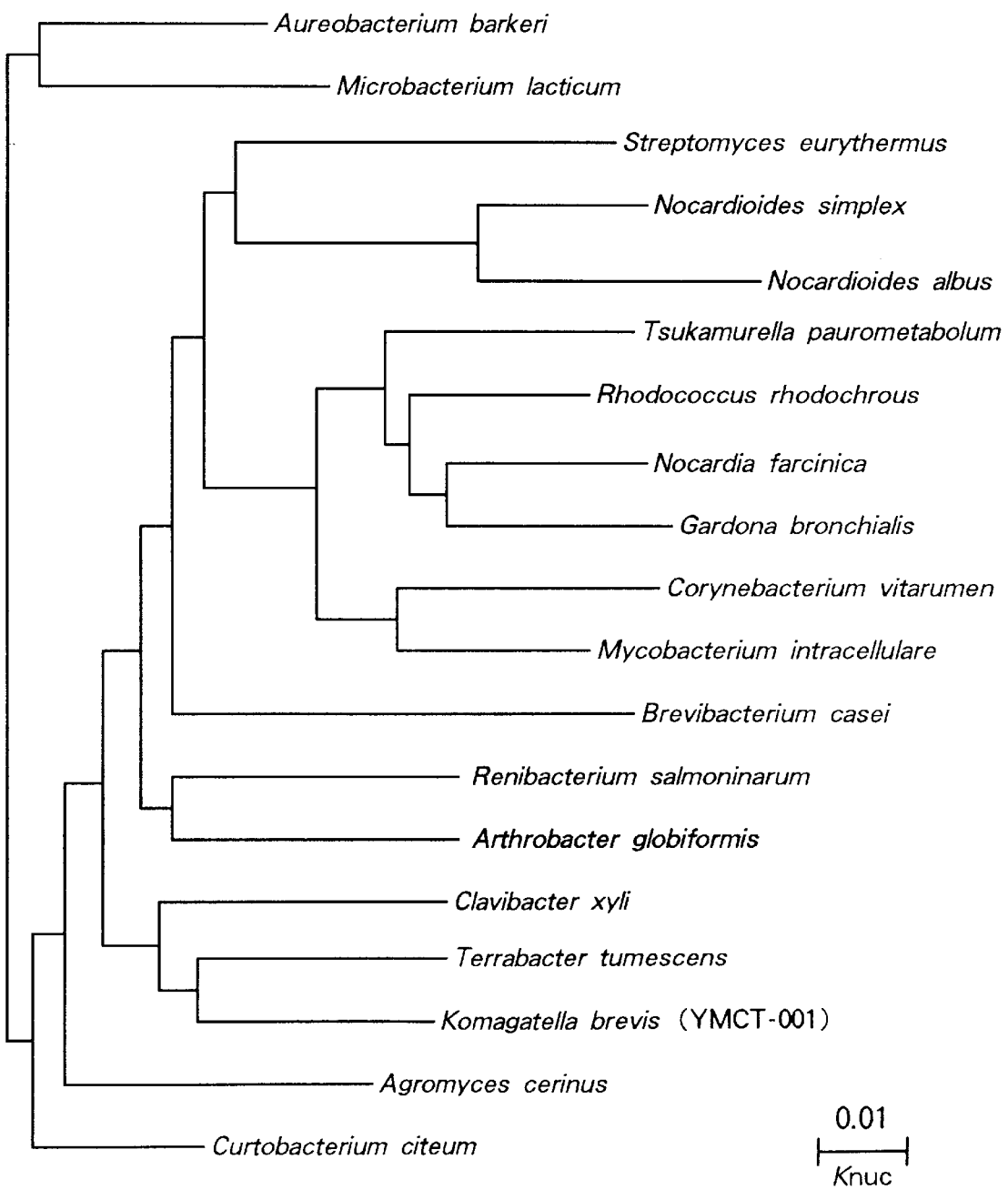
FIG. 3 is a molecular genealogical tree obtained by a neighbor-joining method (NJ method).

In order to classify in view of genetic properties, the nucleotide sequence of 16S rRNA of the strain YMCT-001 was determined and the above-described bacteriological properties were taken into consideration. The nucleotide sequence of 16S rRNA of the strain YMCT-001 was compared with the nucleotide sequence of 16S rRNA of a bacteria which was considered to be relate to the strain YMCT-001. And, a molecular genealogical tree was prepared by the NJ method by using Gene Works (Teijin System Technology Kabushiki Kaisha). FIG. 3 shows the obtained molecular genealogical tree.

As shown in FIG. 3, the strain YMCT-001 was found to be closely related with bacteria belonging to Terrabacter by the analysis of a gene, but it was suggested by examining in view of an evolutional distance that the strain YMCT-001 was closely related with Terrabacter but a bacterium belonging to a different genus. In FIG. 3, the branch length of the molecular genealogical tree is proportional to a probable base substitution number, and the bar scale denotes an evolutional distance. When examined in view of the bacteriological properties of the strain YMCT-001 and the bacteria belonging to Terrabacter, diamino acid of the cell wall was meso-diaminopimelic acid for the strain YMCT-001, while diamino acid of the cell wall was LL-diaminopimelic acid for the bacteria belonging to Terrabacter as shown in the above (e) Chemical taxonomical properties, resulting in that the types of diamino acid of the cell wall were different. The type of diamino acid in the cell wall is one of the indexes for taxonomically classifying genus.

Therefore, the inventors concluded in view of the evolutional distance of the strain YMCT-001 with respect to Terrabacter and the bacteriological properties of the strain YMCT-001 that the strain YMCT-001 was appropriately classified as a new species very closely related to Terrabacter. They judged that the strain YMCT-001 was a new kind of bacteria belonging to a new genus and named it as *Komagatella brevis*.

Accordingly, bacteriological properties of *Komagatella brevis* and others were examined in view of a genetical distance. Bacteria with a relatively close genetical distance were examined whether or not they have the same properties as *Komagatella brevis*. The obtained results are shown in the above-described Table 1. It is apparent from this table that they have the same properties as Arthrobacter, Brevibacter, Clavibacter, Mycobacterium, Renibacterium, Terrabacter and Komagatella. FIG. 3 shows that the genetical distances of the above genera from Komagatella.

As to the culture of the strain YMCT-001, it can be grown at a temperature of 277K to 313K, but the culture temperature is preferably 283 to 303K, and most preferably 288 to 298K. And, the culture medium has a pH value of 6.0 to 9.5, and preferably 6.5 to 9.0. The most suitable pH value of the culture medium for the culture is 7.5 to 8.5. The culture medium for growing the strain YMCT-001 may be an LB culture medium, an NB culture medium or the like for general bacteria, and various kinds of inorganic salts culture medium.

The strain YMCT-001 can be grown with TCE, cis-DCE, trans-DCE, 1,1-DCE or the like as the sole carbon source, and has the decomposing ability against various types of organic compounds such as tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichloro-hexafluoro-2-butene, dichlorobenzene, trichlorobenzene, bromobenzene, 1-bromonaphthalene and polychlorinated biphenyl. Therefore, the strain YMCT-001 can be used effectively and extensively in the cleanup and decomposition treatments of the environments contaminated by organic compounds by microorganisms, and excels in practical use. And, by applying the strain YMCT-001 to a bioreactor and adjusting the number of bacteria, organic compounds in a higher concentration can be decomposed more efficiently. Since the strain YMCT-001 satisfactorily decomposes organic compounds at a pH value of 6.0 to 8.5, and a temperature of 283 to 303K, to apply the strain YMCT-001 to the bioreactor, it is preferable to control the bacteria bed in the bioreactor to a pH value of 6.0 to 8.5, and a temperature of 283 to 303K.

Specific embodiments of the invention will be described below.

EMBODIMENT 1

First, 25 mL of the above-described inorganic salts culture medium and bacterial cells from 100 μL ($OD_{660}$=1.0) of an LB liquid culture medium for the strain YMCT-001 were placed in a vial, and this vial was prepared in plural numbers. And, TCE, cis-DCE, and trans-DCE were added in a concentration of 1 ppm into the respective vials. They were subjected to the shaking culture under conditions of 298K and 100 rpm, and the change of the concentration of each organic compound with time was measured by a gas chromatography. The obtained results are shown in FIG. 4.

Figure 4:
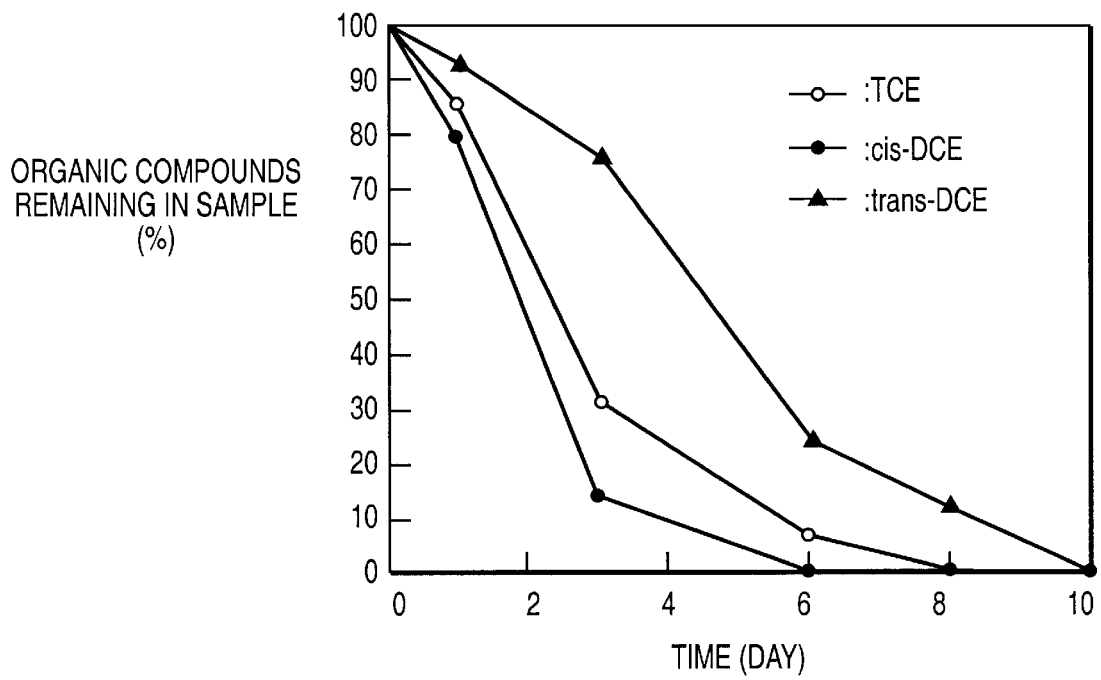
FIG. 4 is a diagram showing the decomposition test result of respective organic compounds using strain YMCT-001 in Embodiment 1.

It is apparent from FIG. 4 that no organic compound came to be detected in 10 days. Besides, the strain YMCT-001 had the decomposing activity on carbon tetrachloride, dichloroethane, trichloroethane, tetrachloroethane, vinyl chloride, tetrachloroethylene, dichlorobenzene, and polychlorinated biphenyl (PCB).

EMBODIMENT 2

First, preparations were made for sample A prepared by placing 25 mL of a inorganic salts culyure medium and bacterial cells from 100 μL ($OD_{660}$=1.0) of an LB liquid culture medium for the strain YMCT-001 in a vial, sample B prepared by placing bacterial cells from 100 μL of a suspension concentrated by a centrifugal force to have the number of bacterial cells 25 times greater than in sample A, sample C prepared by placing bacterial cells from 100 μL of a suspension concentrated by a centrifugal force to have the number of bacterial cells 100 times greater than in sample A, and sample D prepared by placing bacterial cells from 100 μL of a suspension diluted to ¼ of the LB liquid culture medium ($OD_{660}$=1.0) used in sample A.

Figure 5:
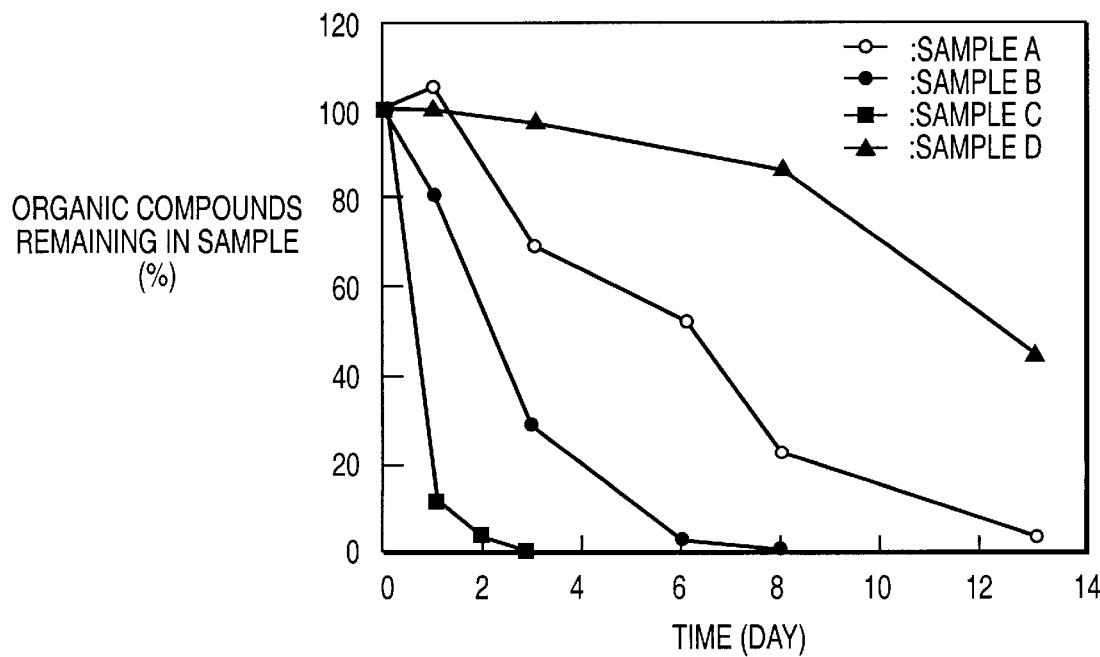
FIG. 5 is a diagram showing the relation between the number of bacteria of strain YMCT-001 and the TCE decomposition rate in Embodiment 2.

TCE was added to the respective samples so as to be a concentration of 1 ppm therein, and subjected to the shaking culture under conditions of 298K and 100 rpm during which the change of the TCE concentration with time was measured. The obtained results are shown in FIG. 5. It is apparent from FIG. 5 that time for the complete decomposition of TCE can be shortened substantially by increasing the number of bacteria in contact with TCE at the start point of decomposition of TCE.

EMBODIMENT 3

Figure 6:
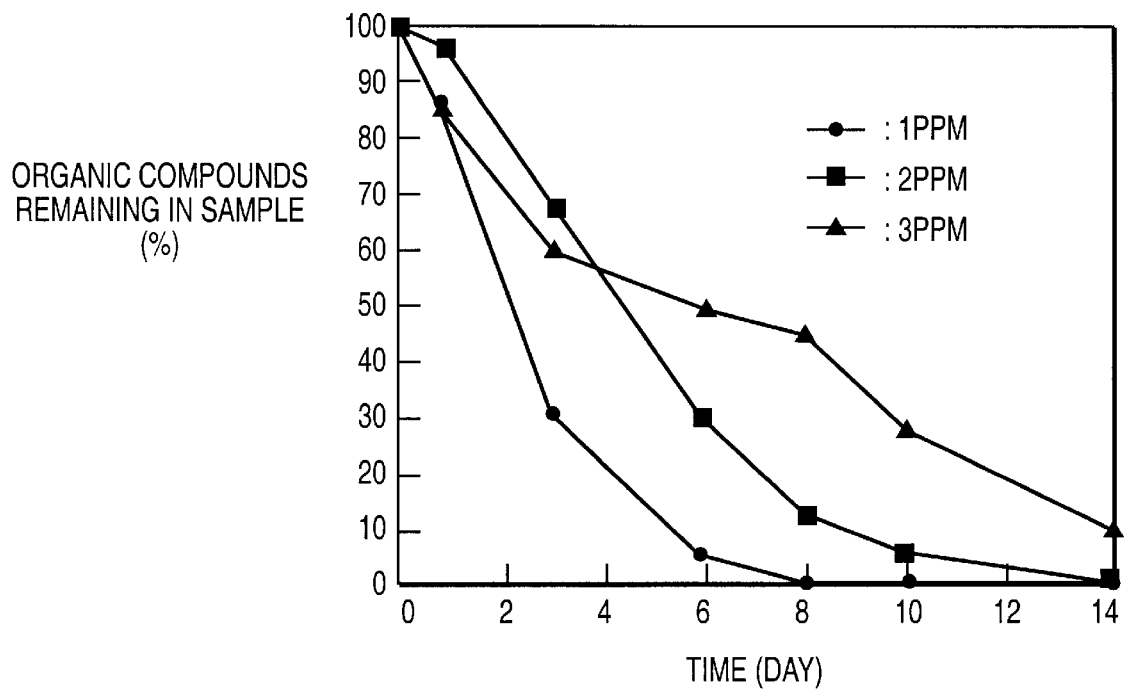
FIG. 6 is a diagram showing the decomposition rate of TCE by strain YMCT-001 with varying concentration of TCE in Embodiment 3.
Figure 7:
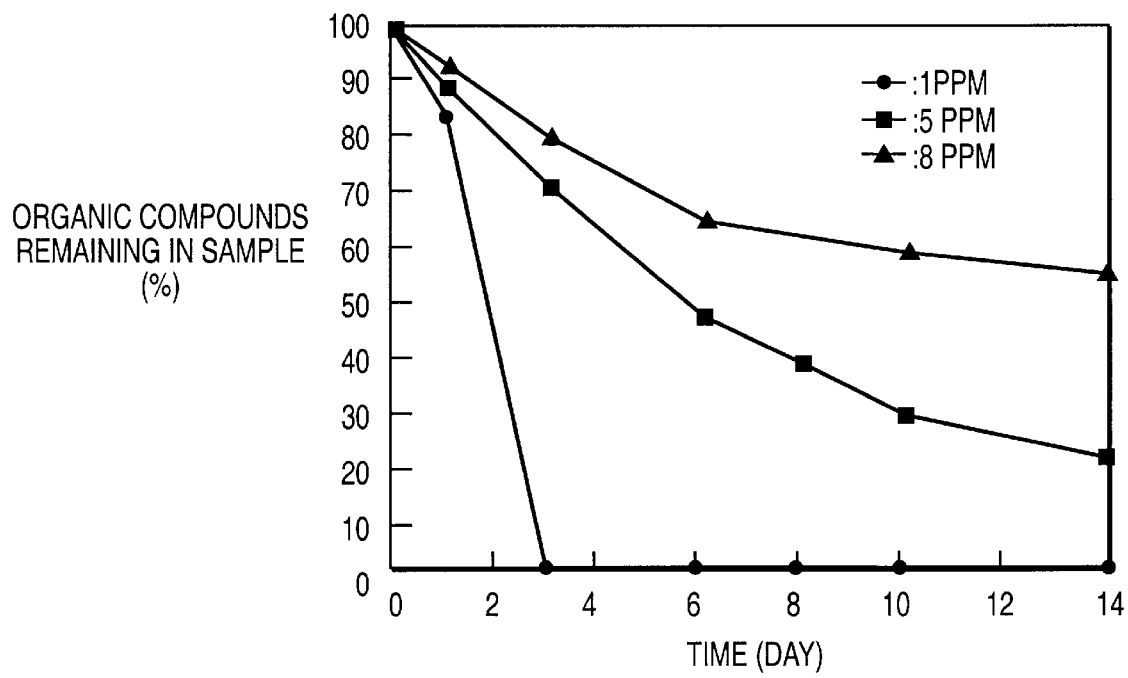
FIG. 7 is a diagram showing the decomposition rate of cis-DCE by strain YMCT-001 with varying concentration of cis-DCE in Embodiment 3.
Figure 8:
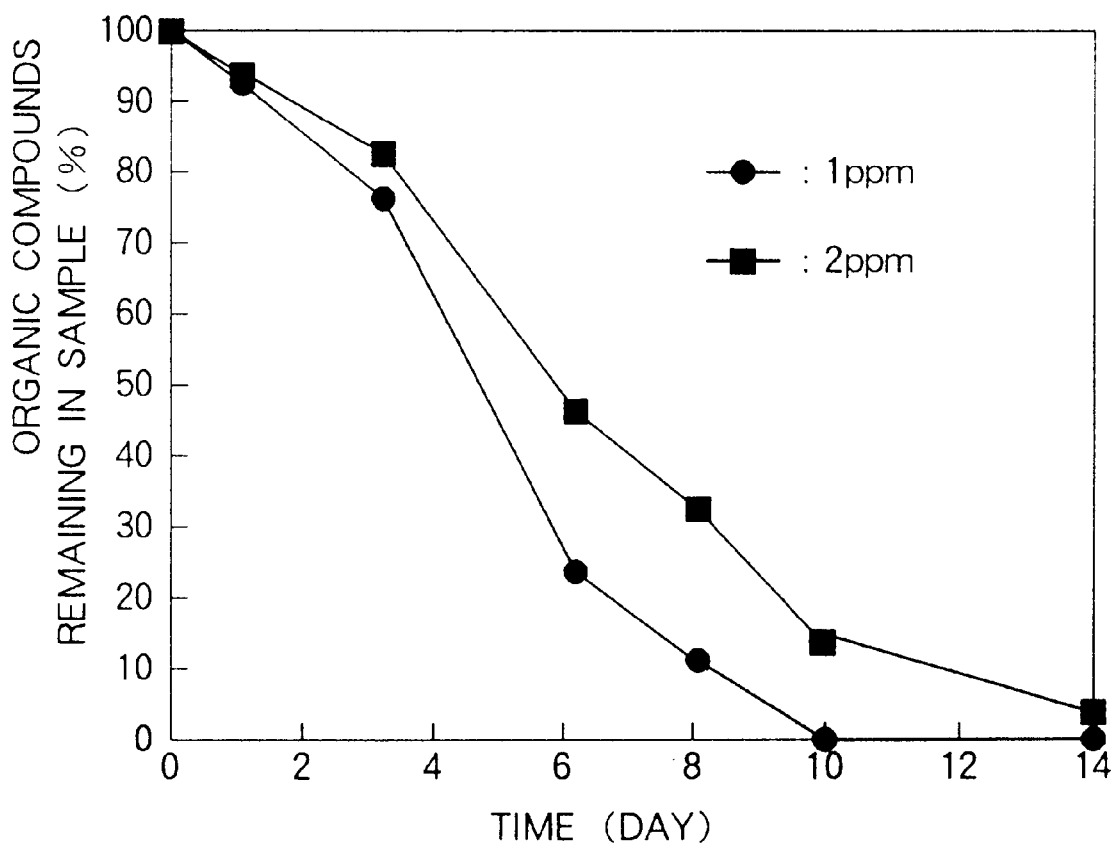
FIG. 8 is a diagram showing the decomposition rate of trans-DCE by strain YMCT-001 with varying concentration of trans-DCE in Embodiment 3.

The decomposition test was conducted in the same way as Embodiment 2 except that the TCE concentration was changed to 1 ppm, 2 ppm and 3 ppm, the cis-DCE concentration to 1 ppm, 5 ppm and 8 ppm, the trans-DCE concentration to 1 ppm and 2 ppm, and bacterial cells from 100 μL of a suspension concentrated to 25 times was added. The obtained results are shown in FIG. 6, FIG. 7 and FIG. 8. It is apparent from these drawings that the strain YMCT-001 has the decomposing ability against a high concentration of organic compounds.

EMBODIMENT 4

First, 25 mL of a inorganic salts culture medium and bacterial cells from 100 μL ($OD_{660}$=1.0) of an LB liquid culture medium for strain YMCT-001 were placed in each vial. And, glucose was added in an amount of 0.18 mg/L, 18 mg/L and 1800 mg/L, 10000 mg/L as total organic carbon (TOC) and a control sample without glucose to prepare samples E, F, G, H and I, respectively.

TCE was added to the respective samples so as to be a concentration of 1 ppm therein, and subjected to the shaking culture under conditions of 298K and 100 rpm during which the change of the TCE concentration with time was measured. The obtained results are shown in FIG. 9.

Figure 9:
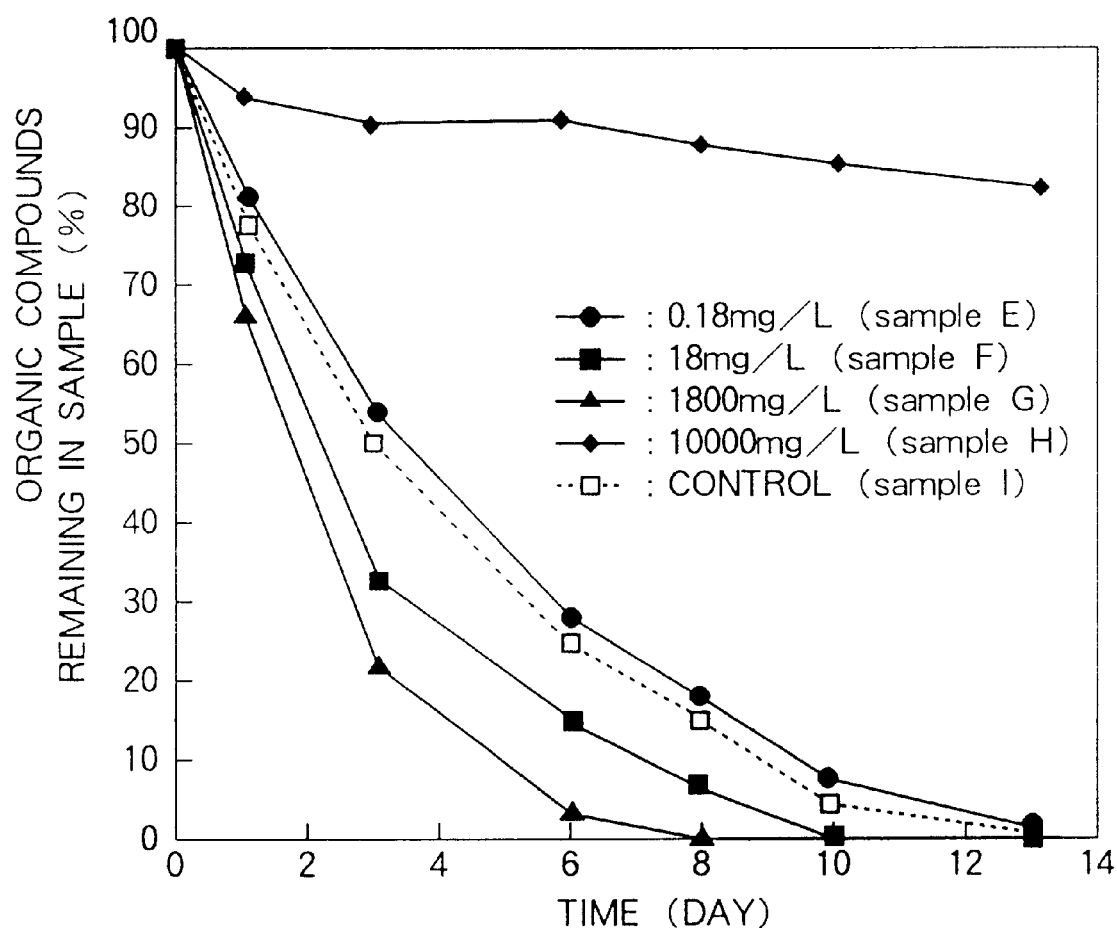
FIG. 9 is a diagram showing the TCE decomposition test result of strain YMCT-001 in the presence of glucose in Embodiment 4.

It is apparent from FIG. 9 that even when TCE and glucose were coexisted, the strain YMCT-001 had a decomposing activity against TCE in the glucose concentration in this embodiment. In addition, it is apparent from FIG. 9 that when glucose exists in the range of 0.18 mg/L to 1800 mg/L as TOC, YMCT-001 shows decomposing ability at the same or to a higher extent as when glucose does not exist.In addition to TCE, the strain YMCT-001 had substantially the same decomposing activity on carbon tetrachloride, dichloroethane, trichloroethane, tetrachloroethane, vinyl chloride, tetrachloroethylene, dichlorobenzene, and polybiphenyl chloride (PCB).

EMBODIMENT 5

A decomposition test was performed on cis-DCE by following the procedure of Embodiment 2 except that a brown forest soil in a volume of 25 mL contaminated by about 100 ppm of cis-DCE (cis-DCE 100 mg/kg soil), 10 mL of a inorganic salts culture medium and bacterial cells from 100 μL ($OD_{660}$=1.0) of an LB liquid culture medium for strain YMCT-001 were placed in a vial (about 4 ppm of concentration in the cis-DCE liquid). As a result, the cis-DCE contained in the soil came not to be detected in 7 days.

EMBODIMENT 6

A decomposition test was performed by following the procedure of Embodiment 2 except that about 2 ppm of cis-DCE, 25 mL of underground water contaminated by about 1 ppm of TCE, and bacterial cells from 100 μL ($OD_{660}$=1.0) of an LB liquid culture medium for strain YMCT-001 were placed in a vial. As a result, the cis-DCE and TCE were not detected in 14 days.

EMBODIMENT 7

Figure 10:
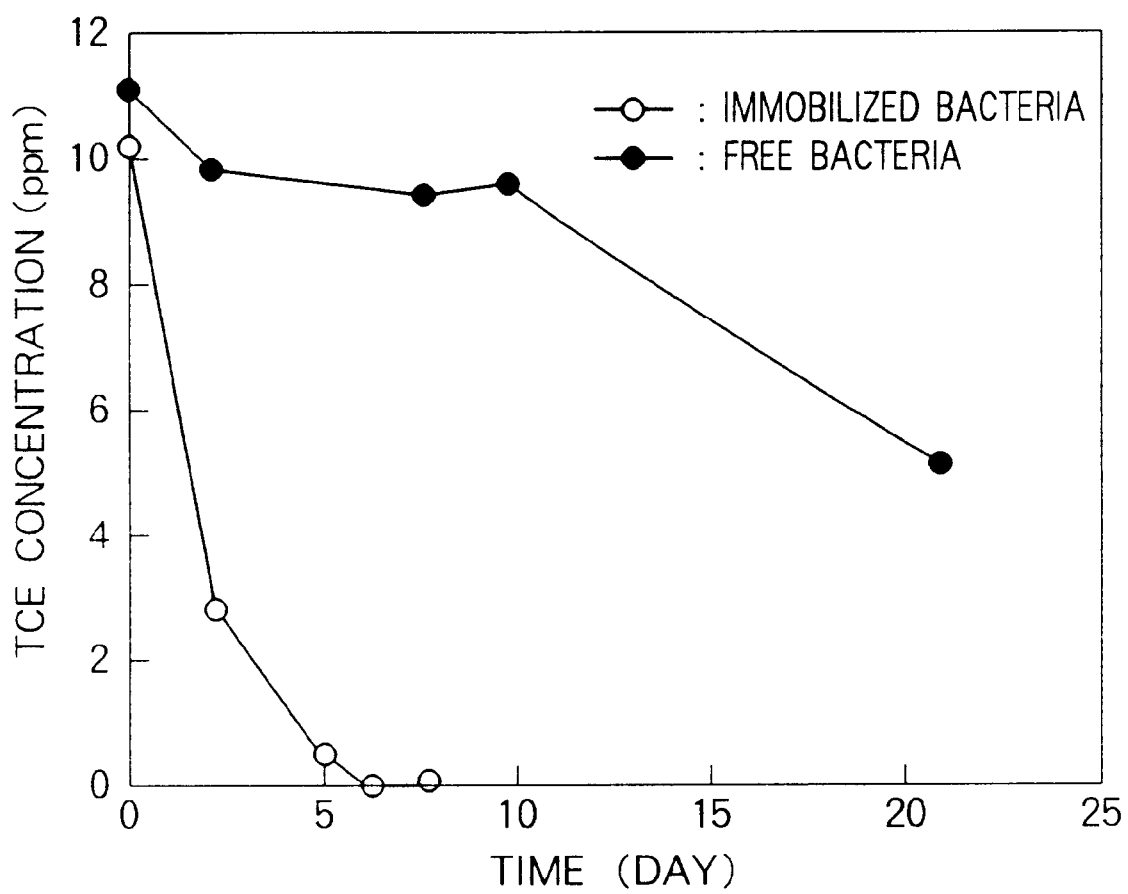
FIG. 10 is a diagram showing the TCE decomposition test results of immobilized cells and free cells in Embodiment 7.

The strain YMCT-001 was held on various types of carriers as immobilized bacteria, and a decomposition test was performed on 10 ppm of TCE. The carriers used are shown in Table 2. FIG. 10 shows an example (carrier: calcium alginate gel) of the decomposition test results on TCE by the immobilized bacteria. Compared with bacteria in a free state, a higher concentration of organic compounds could be decomposed in a short time by using the immobilized bacteria which could contact a large amount of bacteria to TCE to be decomposed.

TABLE 2

Carriers materials for fixing strain YMCT-001

| | |
|---|---|
| Gel | Calcium alginate gel |
| | Agarose gel |
| | Carrageenan gel |
| Inorganic material | Porous alumina ceramics |
| | Porous silica ceramics |
| | single-crystal alumina |
| | Single-crystal silica |
| | Glass beads |
| Organic material | Collagen |
| | Fibroin |
| | Chitin |
| | Chitosan |
| Synthetic resin | Polyethylene stereoreticular body |
| | Polypropylene stereoreticular body |
| | Polyurethane |
| | Photo-setting resin |
| | Polyelectrolyte composite |

EMBODIMENT 8

Teflon filter paper was immersed in a suspension of the strain YMCT-001 ($OD_{660}=1.0$) to make the shaking culture at 25° C. for 18 hours. Then, the pressure was decreased to carry the strain YMCT-001 into the filter paper. Since water was contained in the filter paper immediately after carrying the strain YMCT-001 therein, the filter was dried to recover water repellency. Thus, teflon filter paper 111 having the strain YMCT-001 carried was prepared.

Figure 11:
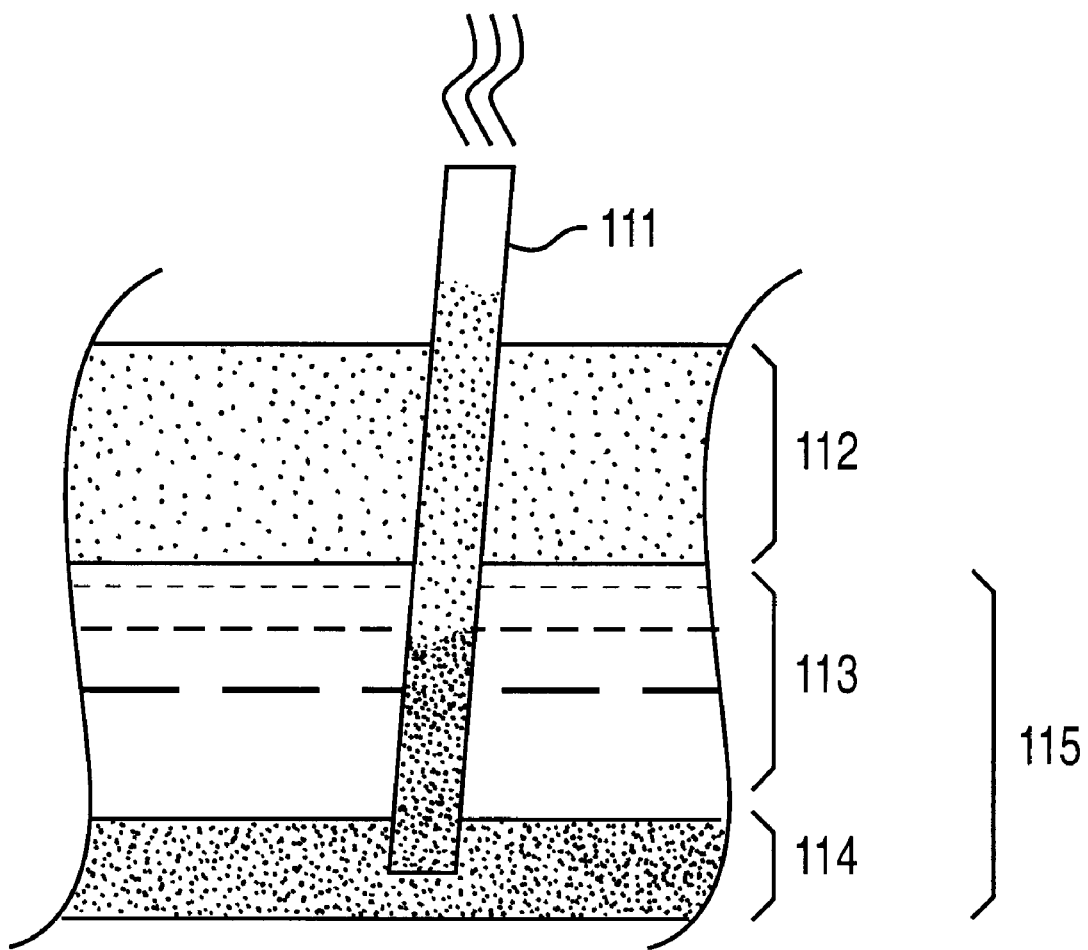
FIG. 11 is a diagram showing the state of decomposing the organic compounds in Embodiment 8.

Meanwhile, soil contaminated by various types of organic compounds was charged into an concrete lysimeter container of 400 cm×400 cm×800 cm. As shown in FIG. 11, the soil charged into the concrete lysimeter container has a saturated area 115 consisting of an unsaturated area 112, a permeable layer 113, and a hard permeable layer 114 like soil in the environment.

The teflon filter paper 111 having the strain YMCT-001 carried was buried into the soil to reach the hard permeable layer 114. The buried state is shown in FIG. 11. As to the concentrations of the organic compounds in the soil, TCE was 5 ppm, toluene 100 ppm, phenol 100 ppm, vinyl fluoride 5 ppm.

Figure 12:
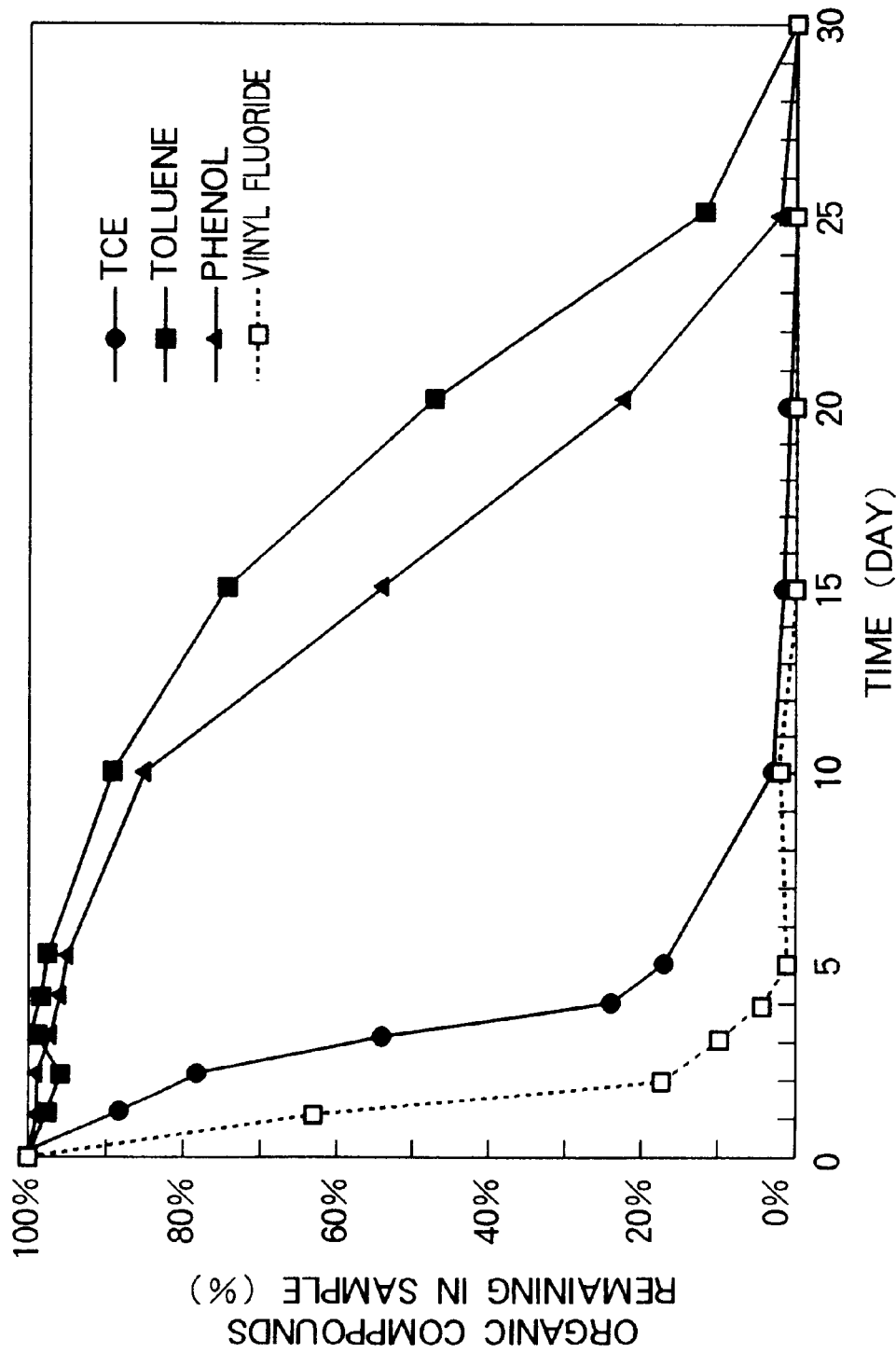
FIG. 12 is a diagram showing the results of decomposing various types of organic compounds using the strain YMCT-001 in Embodiment 8.

And, after burying the teflon filter paper 111 having the strain YMCT-001 carried into the soil, the top of the concrete lysimeter container was closed and sealed with a resin. The soil was sampled with the elapse of time to measure the concentration of each organic compound contained in the soil. The results are shown in FIG. 12. The soil was kept at 15° C.

It is apparent from FIG. 12 that all organic compounds in various types contained in the soil could be decomposed completely in this embodiment.

EMBODIMENT 9

Figure 13:
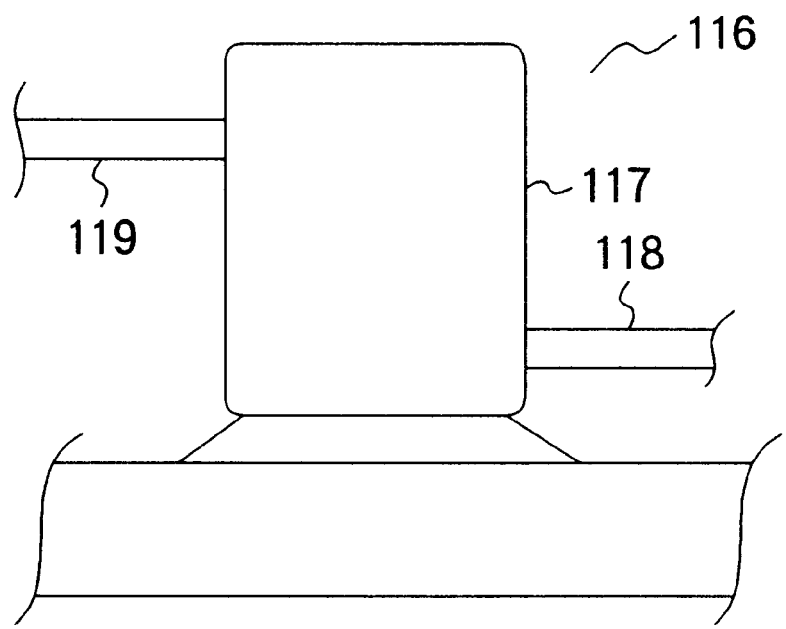
FIG. 13 is a diagram showing the state of decomposing the organic compounds in Embodiment 9.

The strain YMCT-001 was charged into a tank 117 of a bioreactor system 116 shown in FIG. 13. And, underground water contaminated by various types of organic compounds was charged into the tank 117 through a supply pipe 118 to decompose the organic compounds by the strain YMCT-001. As to the initial concentrations of the organic compounds in the underground water, TCE was 5 ppm, toluene 100 ppm, phenol 100 ppm, and vinyl fluoride 1 ppm. And, the tank 117 had a capacity of 2000 L, its inner temperature was retained at 25° C., and it was designed that the underground water which had the contained organic compounds decomposed was discharged outside through an outlet pipe 119. The concentration of each organic compound before and after charging into the bioreactor system 116 was measured. The results are shown in FIG. 14.

Figure 14:
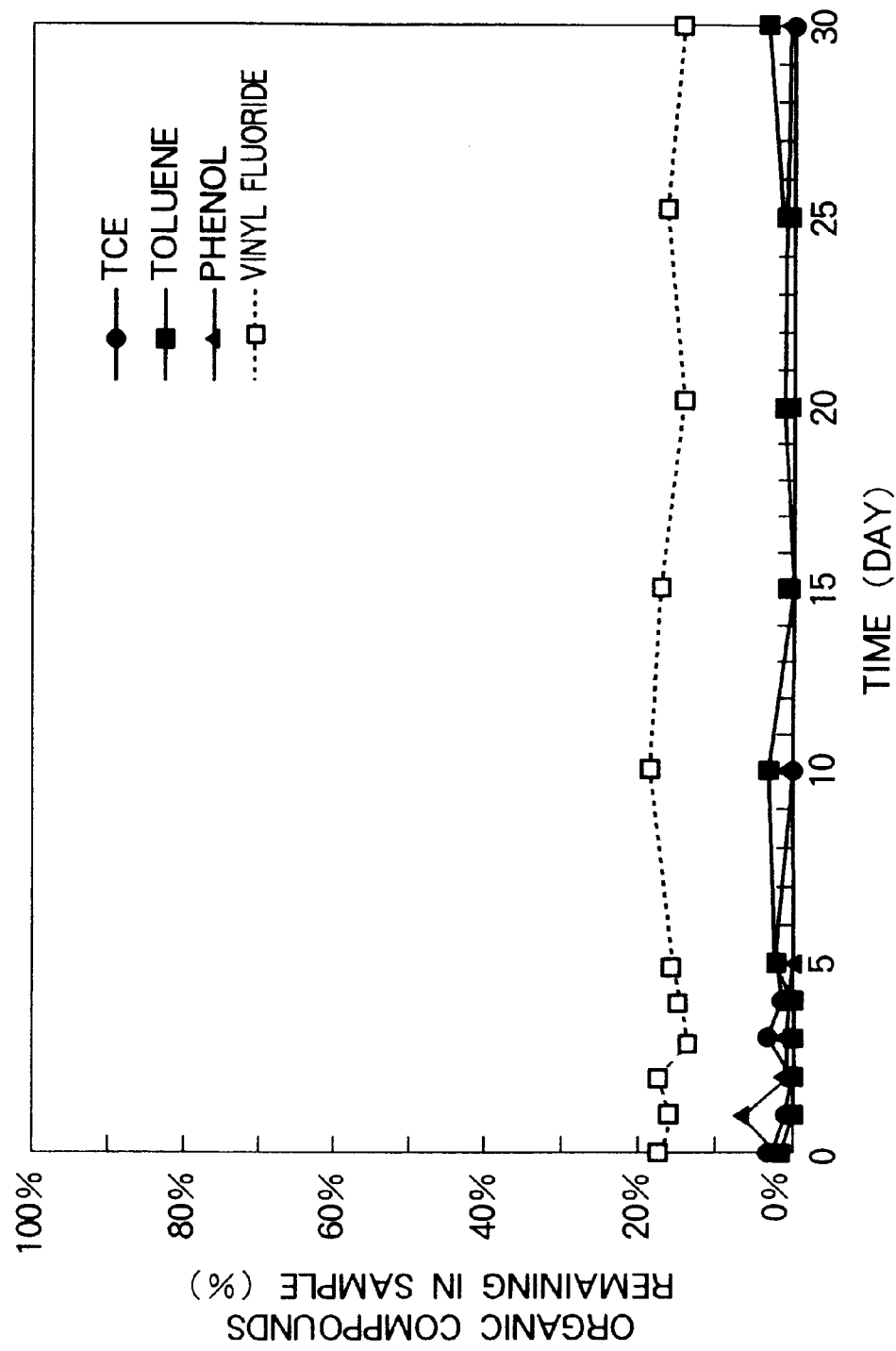
FIG. 14 is a diagram showing the results of decomposing various types of organic compounds using the strain YMCT-001 in Embodiment 9.

It is apparent from FIG. 14 that all organic compounds in various types contained in the underground water could be decomposed completely and stably in this embodiment. Especially, the efficiency of decomposing TCE, toluene and phenol was very good.

EMBODIMENT 10

Figure 15:
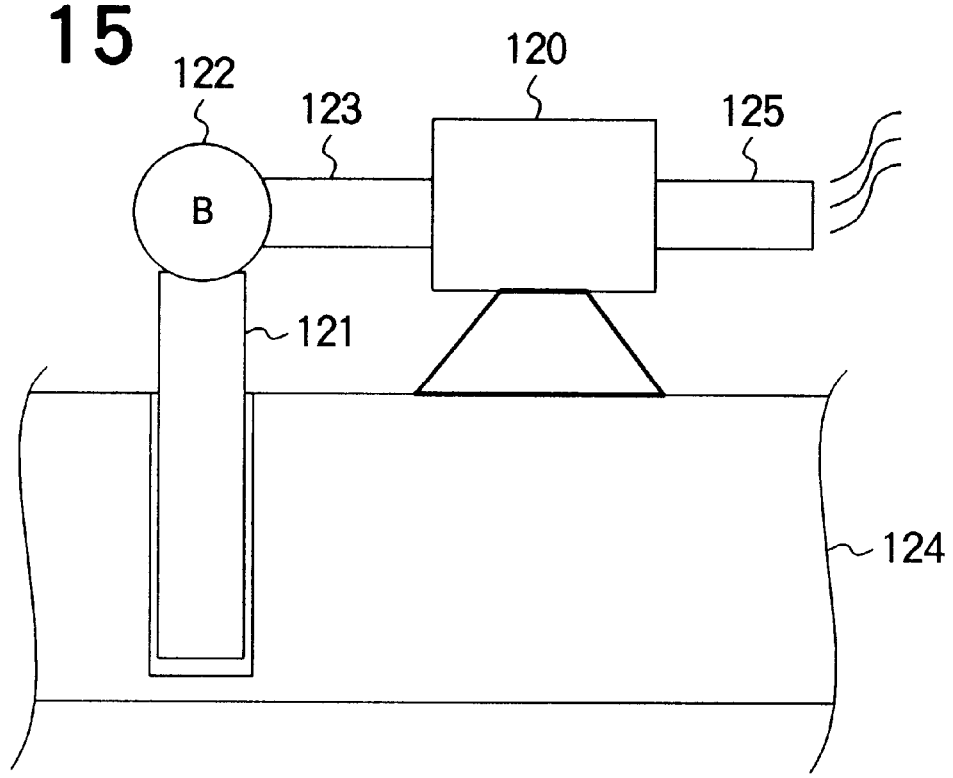
FIG. 15 is a diagram showing the state of decomposing the organic compounds in Embodiment 10.

After carrying the strain YMCT-001 on activated carbon having a particle diameter of about 5 mm, the activated carbon carrying the strain YMCT-001 was charged into a drum having an inner capacity of 1000 mL to prepare a biofilter 120. A gas containing cis-DCE and vinyl fluoride in a concentration of about 1.2 $g/m^3$ was introduced from soil 124 into the biofilter 120 through an insertion pipe 121, a blower 122, and a supply pipe 123 as shown in FIG. 15. And, the concentration of each organic compound before and after charging into the biofilter 120 was measured. The temperature in the biofilter 120 was retained at 25° C., and it was designed that the gas which had the contained organic compounds decomposed was discharged outside through an outlet pipe 125. The results are shown in FIG. 16.

Figure 16:
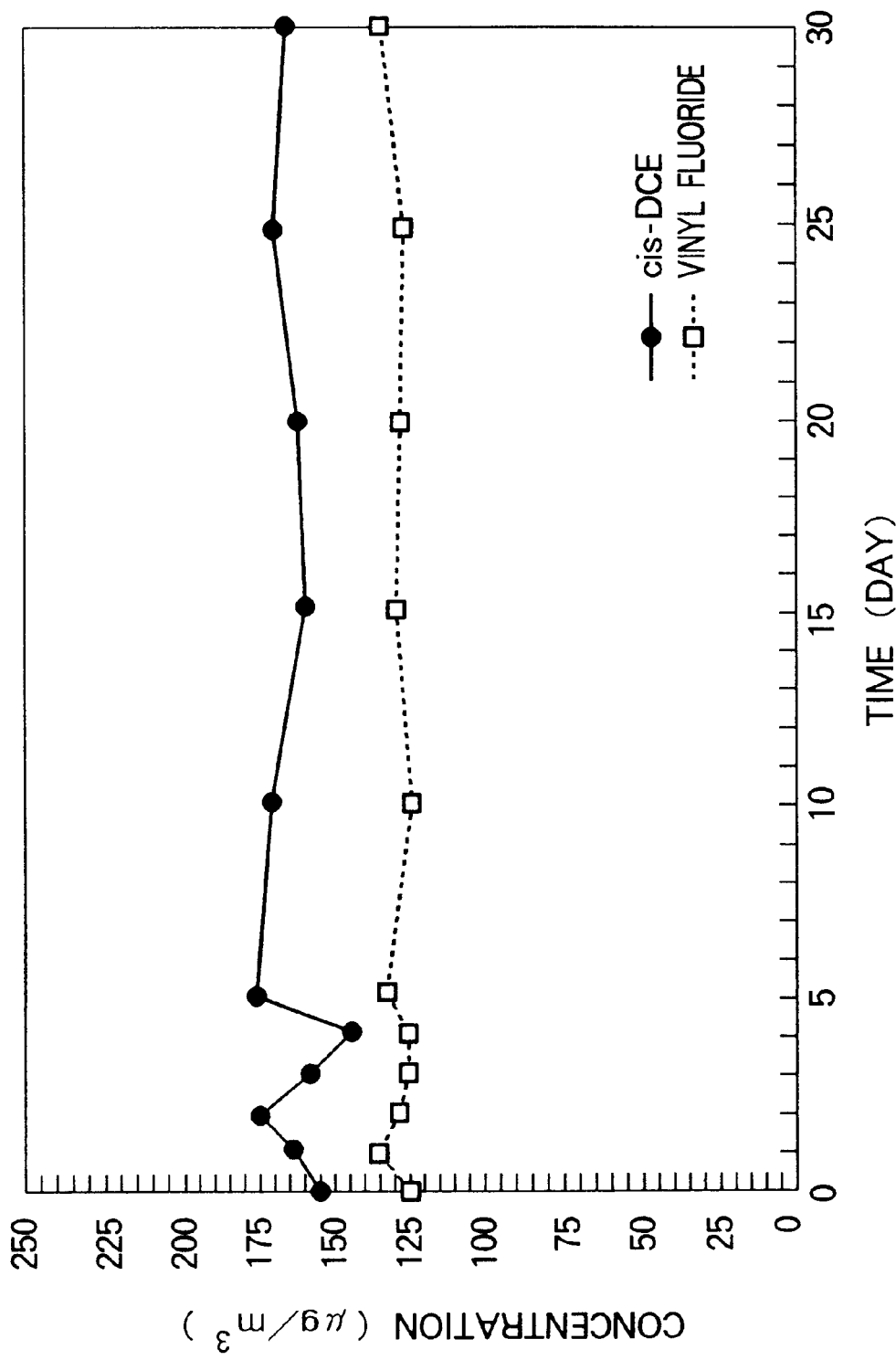
FIG. 16 is a diagram showing the results of decomposing various types of organic compounds using the strain YMCT-001 in Embodiment 10.

It is apparent from FIG. 16 that all organic compounds in various types contained in the underground water could be decomposed completely and stably in this embodiment.

In this embodiment that the strain YMCT-001 was carried on the activated carbon, it took 88 days to break through the activated carbon, but when the strain YMCT-001 was not carried on the activated carbon, it took 28 days to break through the activated carbon. Therefore, the organic compounds could be decomposed stably and completely for a long period in this embodiment.

EMBODIMENT 11

Figure 17:
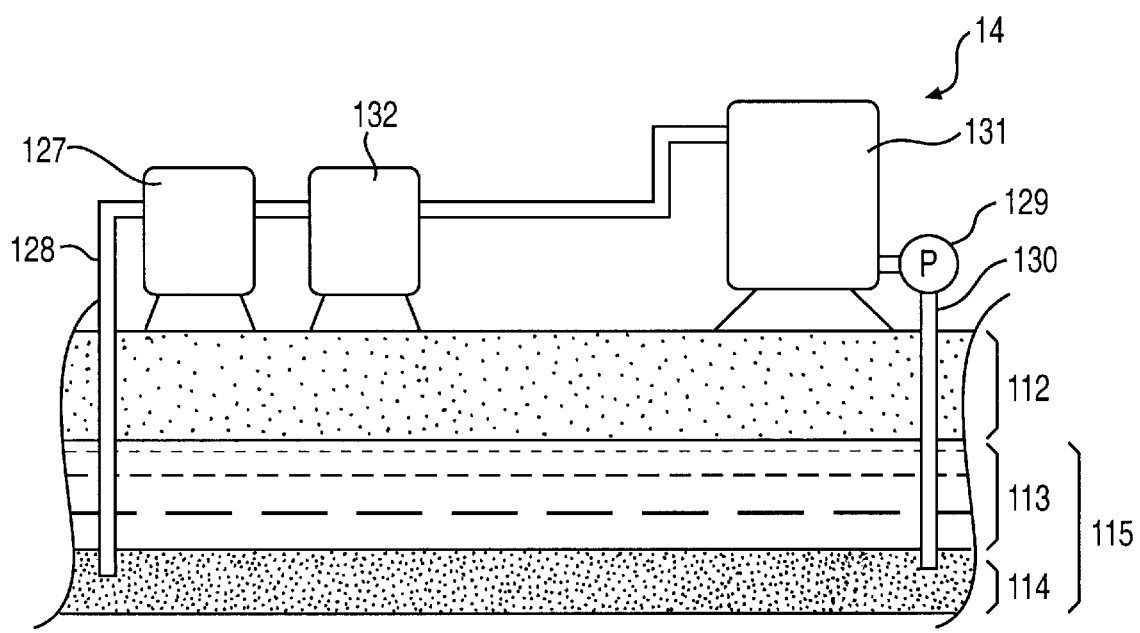
FIG. 17 is a diagram showing the state of decomposing the organic compounds in Embodiment 11.

Soil contaminated by various types of organic compounds was charged into a lysimeter container of 400 cm×400 cm×800 cm, and a pumped water circulating system 126 was prepared as shown in FIG. 17. The soil charged into the lysimeter container has a saturated area 115 consisting of an unsaturated area 112, a permeable layer 113, and a hard permeable layer 114 like soil in the environment. And, as to the initial concentrations of the organic compounds in the soil, TCE was 5 ppm, toluene 100 ppm, phenol 100 ppm, and vinyl fluoride 1 ppm. The pumped water was circulated at a rate of 1 m/day. The top of the lysimeter container was closed and airtightly sealed with a resin. The strain YMCT-001 was injected into the soil from a microorganism supply device 127 through a supply pipe 128 to have a bacterial cell concentration of $10^8$ cfu per 1 mL of soil. The underground water was pumped by a pump 129 through a feed pipe 130 and flown within the pumped water circulating system 126. But, activated carbon was not charged into an activated carbon adsorption tower 131, and a substance such as glucose was not added from a supply device 132 in this embodiment. The soil temperature was kept at 15° C. The concentration of each organic compound contained in the underground water flown through the soil was measured. The results obtained are shown in FIG. 18.

Figure 18:
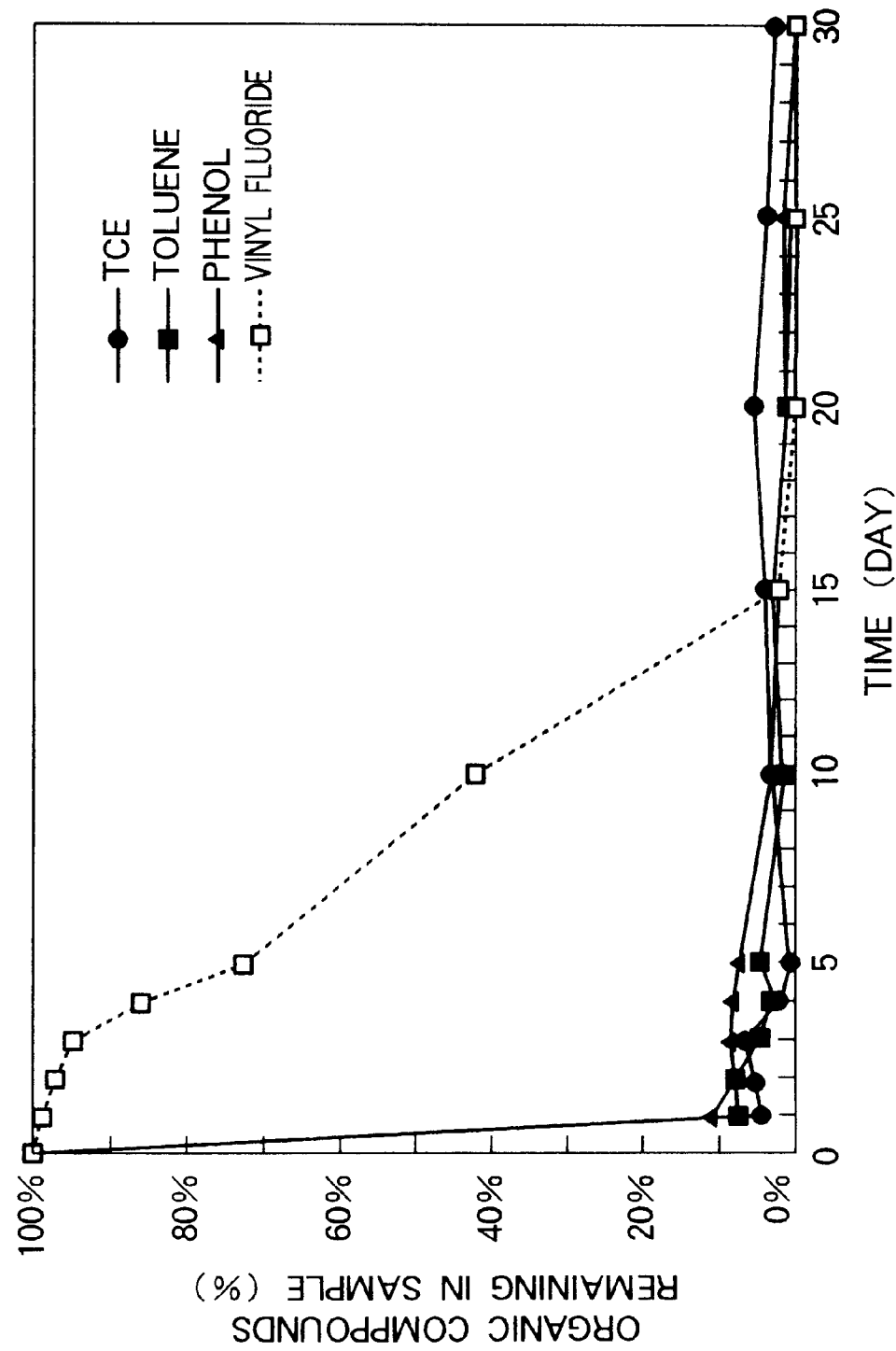
FIG. 18 is a diagram showing the results of decomposing various types of organic compounds using the strain YMCT-001 in Embodiment 11.

It is apparent from FIG. 18 that all organic compounds in various types contained in the underground water could be decomposed completely and stably in this embodiment.

EMBODIMENT 12

Soil contaminated by various types of organic compounds was charged into a lysimeter container of 400 cm×400 cm×800 cm, and clean underground water was pumped and circulated at a rate of 0.01 m/day. The soil charged into the lysimeter container has a saturated area 115 consisting of an unsaturated area 112, a permeable layer 113, and a hard permeable layer 114 like soil in the environment. And, as to the initial concentrations of the organic compounds in the soil, TCE was 5 ppm, toluene 100 ppm, phenol 100 ppm, and vinyl fluoride 1 ppm. The top of the lysimeter container was closed and airtightly sealed with a resin.

Figure 19:
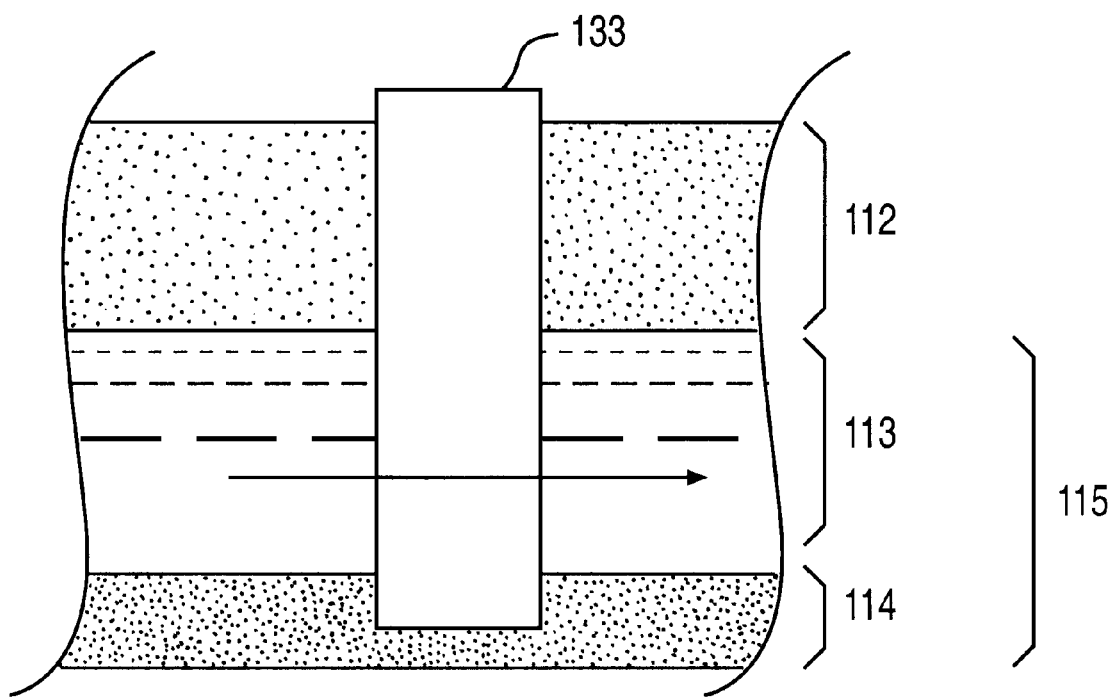
FIG. 19 is a diagram showing the state of decomposing the organic compounds in Embodiment 12.

And, a cylinder 133, in which a ceramics porous substance having a particle diameter of about 5 mm and carrying the strain YMCT-001 was charged, was buried in the soil. The buried state is shown in FIG. 19. The concentration of each organic compound contained in the underground water flown through the soil was measured. The results obtained are shown in FIG. 20.

Figure 20:
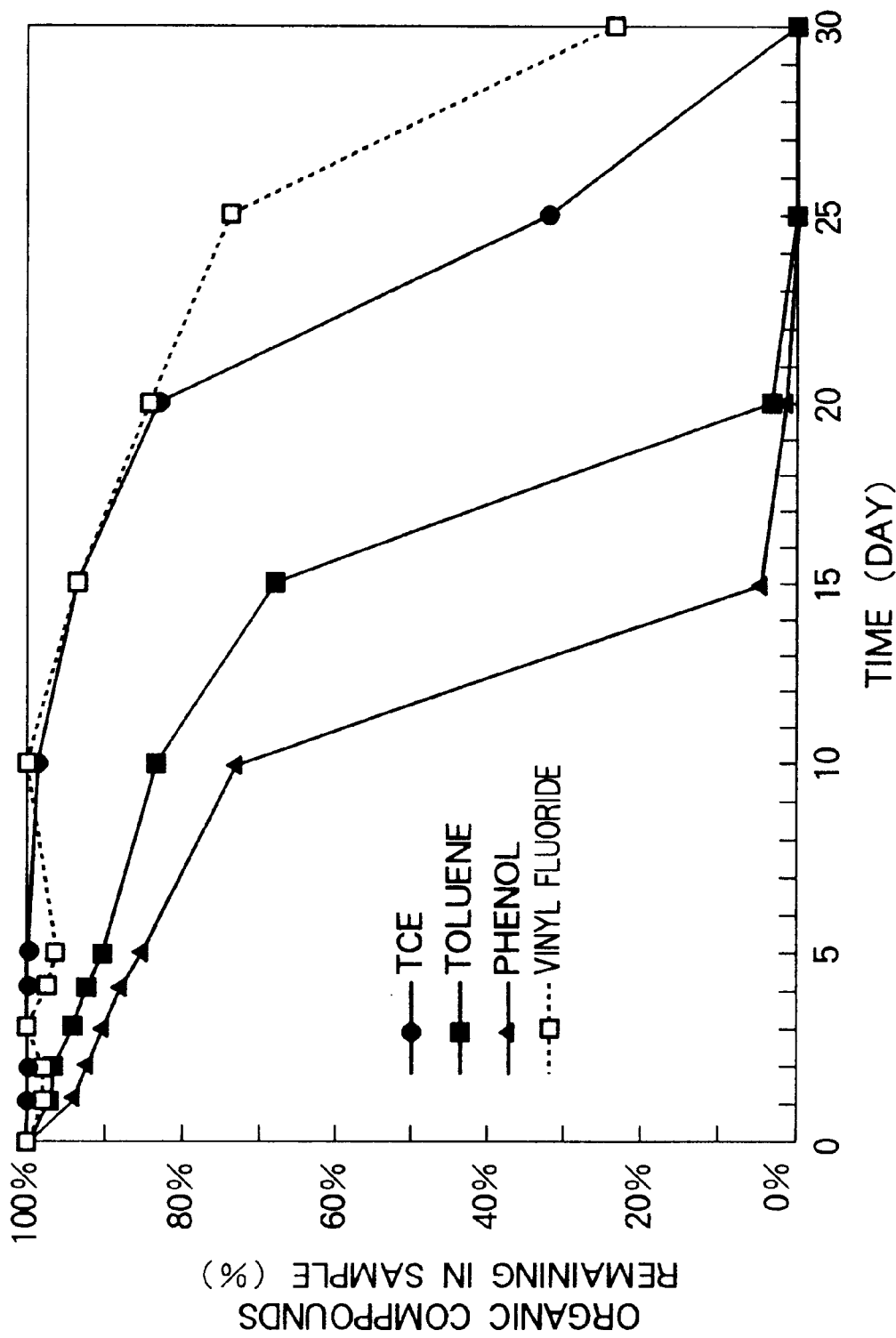
FIG. 20 is a diagram showing the results of decomposing various types of organic compounds using the strain YMCT-001 in Embodiment 12.

It is apparent from FIG. 20 that all organic compounds in various types contained in the underground water could be decomposed completely and stably in this embodiment. The soil temperature was kept at 15° C.

EMBODIMENT 13

Figure 21:
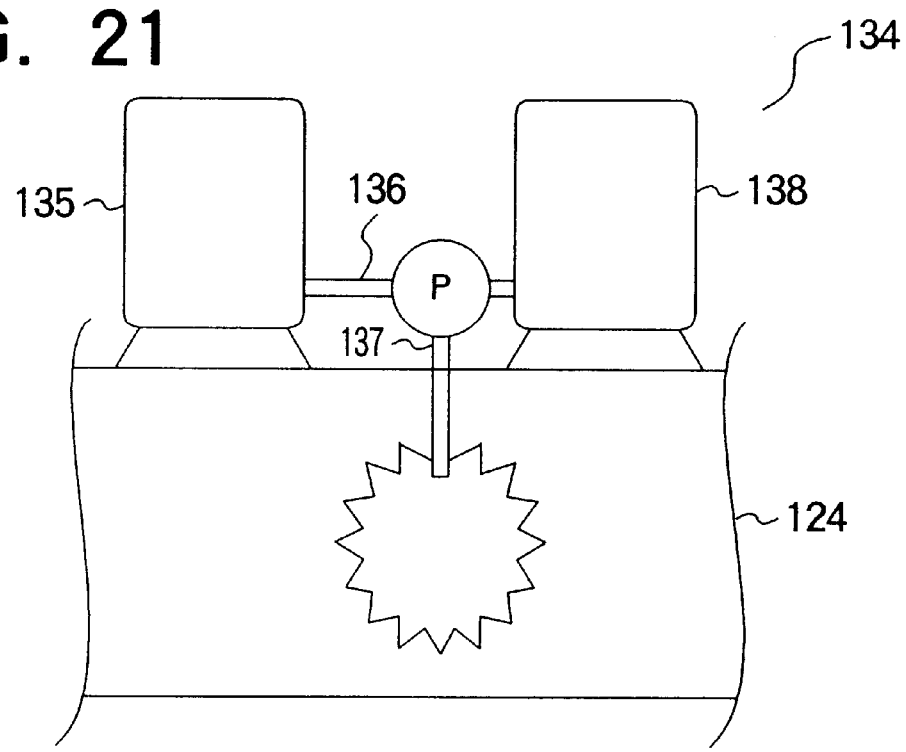
FIG. 21 is a diagram showing the state of decomposing the organic compounds in Embodiment 13.

Soil contaminated by various types of organic compounds was charged into a lysimeter container of 400 cm×400 cm×800 cm, and a purification system 134 was prepared as shown in FIG. 21. As to the initial concentrations of the organic compounds in the soil, TCE was 5 ppm, toluene 100 ppm, phenol 100 ppm, and vinyl fluoride 1 ppm. The strain YMCT-001 was injected into the soil from a microorganism supply device 135 through a supply pipe 136 and an insertion pipe 137 to have a bacterial cell concentration of $10^8$ cfu per 1 mL of soil. A substance such as glucose was not added from a supply device 138.

Figure 22:
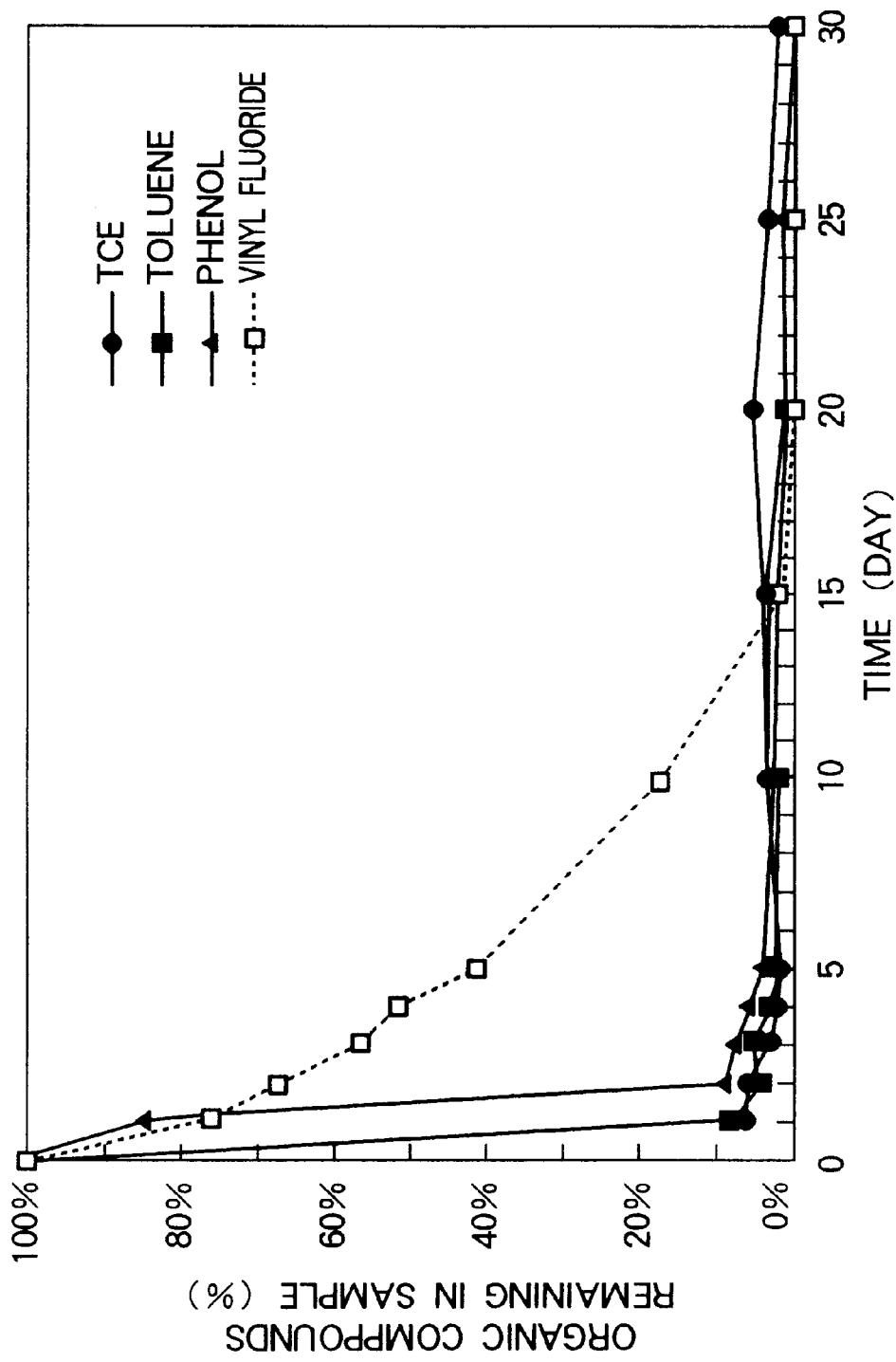
FIG. 22 is a diagram showing the results of decomposing various types of organic compounds using the strain YMCT-001 in Embodiment 13.

After injecting the strain YMCT-001 into the soil, the top of the lysimeter container was closed and airtightly sealed with a resin. The soil was sampled with the elapse of time to measure the concentration of each organic compound contained in the soil. The results are shown in FIG. 22. The soil temperature was kept at 15° C.

It is apparent from FIG. 22 that all organic compounds in various types contained in the soil could be decomposed completely in this embodiment.

As described above, according to the method for decomposing organic compounds according to the present invention, the organic compounds can be decomposed safely and effectively by using the microorganisms having the organic compound decomposing power which are isolated from the contaminated environment with the organic compound tolerance without requiring any additive, inducer or mutagenized bacteria hazardous to the environment. Therefore, the contaminated soil or contaminated underground water can be restored to the original state in situ without causing secondary contamination. And, since the microorganism itself is derived from the contaminated environment, the microorganism has no possibility of causing the secondary contamination.

The apparatus for decomposing organic compounds according to the invention is structured to decompose the organic compounds by the microorganisms having the organic compound decomposing ability which are isolated from the contaminated environment with the organic compound tolerance as an index, so that the organic compounds can be decomposed safely and effectively without using any additive, inducer or mutagenized bacteria hazardous to the environment. Therefore, the contaminated soil or contaminated underground water can be restored to the original state without causing secondary contamination. And, since the microorganism itself is derived from the contaminated environment, the microorganism has no possibility of causing the secondary contamination.

And, according to the method for isolating microorganisms of the present invention, the microorganisms effective for biodegradation of organic compounds can be isolated effectively.

Besides, the new microorganism of the present invention efficiently decomposes various kinds of organic compounds without requiring any additive or inducer hazardous to the environment. Therefore, a practical environment restoring technique can be provided.

What is claimed is:

1. A method for microbially decomposing organic compounds comprising the steps of:

collecting a microorganism from an environment contaminated by a first organic compound or a sample contacted to said environment;

culturing the collected microorganism in the environment contaminated by the organic compound so that the microorganism's organic compound tolerance is used as an index of decomposing ability;

selecting said cultured microorganism;

reselecting said selected microorganism based on the organic compound decomposing ability thereof;

contacting said reselected microorganism to the first and/or a second organic compound to form a colony of the microorganism in the environment; and decomposing said first and/or said second organic compound by said microorganism.

2. A method for microbially decomposing organic compounds comprising the steps of:

collecting a microorganism from an environment contaminated by a first organic compound or a sample contacted to said environment;

culturing said collected microorganism with said first organic compound in the environment contaminated by the organic compound;

selecting said cultured microorganism;

reselecting said selected microorganism based on the organic compound decomposing ability thereof;

contacting said reselected microorganism to the first and/or a second organic compound to form a colony of the microorganism in the environment; and decomposing said first and/or said second organic compound by said microorganism.

3. The method according to claim 1 or 2, wherein said microorganism grows with an organic compound as the carbon source.

4. The method according to claim 3, wherein said organic compound is a halogenated hydrocarbon and/or an aromatic hydrocarbon.

5. The method according to claim 4, wherein said halogenated hydrocarbon is trichloroethylene, cis-dichloroethylene, trans-dichloroethylene, 1,1-dichloroethylene, tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichlorohexafluoro-2-butene, or mixtures thereof; and said aromatic hydrocarbon is dichlorobenzene, trichlorobenzene, bromobenzene, 1-bromonaphthalene polychlorinated biphenyl, or mixtures thereof.

6. The method according to claim 2, wherein said microorganism is YMCT-001 (FERM BP-5382).

7. The method according to claim 1 or 2, wherein said first organic compound is a halogenated hydrocarbon and/or an aromatic hydrocarbon.

8. The method according to claim 7, wherein said halogenated hydrocarbon is trichloroethylene, cis-dichloroethylene, trans-dichloroethylene, 1,1-dichloroethylene, tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichlorohexafluoro-2-butene, or mixtures thereof; and said aromatic hydrocarbon is dichlorobenzene, trichlorobenzene, bromobenzene, 1-bromonaphthaline polychlorinated biphenyl, or mixtures thereof.

9. The method according to claim 1 or 2, wherein said second organic compound is a halogenated hydrocarbon and/or an aromatic hydrocarbon.

10. The method according to claim 9, wherein said halogenated hydrocarbon is trichloroethylene, cis-dichloroethylene, trans-dichloroethylene, 1,1-dichloroethylene, tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichlorohexafluoro-2-butene, or mixtures thereof; and said aromatic hydrocarbon is dichlorobenzene, trichlorobenzene, bromobenzene, 1-bromonaphthalene polychlorinated biphenyl, or mixtures thereof.

11. The method according to claim 2, wherein said culturing step is performed under a condition that a gaseous phase concentration of the organic compound is 50 to 10000 ppm.

12. The method according to claim 2, wherein said culturing step is performed using a solid culture medium under a condition that a gaseous phase concentration of the organic compound is 50 to 10000 ppm.

13. The method according to claim 2, wherein said culturing step is performed under the conditions of a temperature of 277 to 313K, a pH value of 6.0 to 8.5, and an oxygen concentration which is saturated under the oxygen partial pressure of 0.2 to 21%.

14. The method according to claim 2, wherein said reselecting step is performed under a condition that a gaseous phase concentration of the organic compound is 50 to 10000 ppm.

15. The method according to claim 2, wherein said reselecting step is performed using a liquid culture medium under a condition that a liquid-phase concentration of the organic compound is not less than 500 ppm.

16. The method according to claim 2, wherein said reselecting step is performed under the conditions of a temperature of 277 to 313K, a pH value of 6.0 to 8.5, and oxygen concentration which is saturated under the oxygen partial pressure of 0.2 to 21%.

17. A method for isolating a microorganism comprising the steps of:
collecting a microorganism from an environment contaminated by at least one organic compound or a sample contacted to said environment;
culturing the collected microorganism in the environment contaminated by the organic compound, so that the microorganism's organic compound tolerance is used as an index of decomposing ability;
selecting said cultured microorganism; and
reselecting said selected microorganism based on an organic compound decomposing ability thereof.

18. A method for isolating a microorganism comprising the steps of:
collecting a microorganism from an environment contaminated by at least one organic compound or a sample contacted to said environment;
culturing the collected microorganism with said organic compound in the environment contaminated by the organic compound;
selecting said cultured microorganism; and
reselecting said selected microorganism based on an organic compound decomposing ability thereof.

19. The method according to claim 17, wherein said microorganism grows with the organic compound as the carbon source.

20. The method according to claim 19, wherein said organic compound is a halogenated hydrocarbon and/or an aromatic hydrocarbon.

21. The method according to claim 20, wherein said halogenated hydrocarbon is trichloroethylene, cis-dichloroethylene, trans-dichloroethylene, 1,1-dichloroethylene, tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichlorohexafluoro-2-butene or mixtures thereof; and said aromatic hydrocarbon is dichlorobenzene, trichlorobenzene, bromobenzene, 1-bromonaphthalene polychlorinated biphenyl or mixtures thereof.

22. The method according to claim 17, wherein said microorganism is YMCT-001 (FERM BP-5282).

23. The method according to claim 17, wherein said organic compound is a halogenated hydrocarbon and/or an aromatic hydrocarbon.

24. The method according to claim 23, wherein said halogenated hydrocarbon is trichloroethylene, cis-dichloroethylene, trans-dichloroethylene, 1,1-dichloroethylene, tetrachloroethylene, dichloroethane, trichloroethane, tetrachloroethane, vinyl chloride, carbon tetrachloride, vinyl fluoride, vinyl bromide, 3,3,3-trifluoro-2-propene, 2,3-dichlorohexafluoro-2-butene or mixtures thereof; and said aromatic hydrocarbon is dichlorobenzene, trichlorobenzene, bromobenzene, 1-bromonaphthalene polychlorinated biphenyl or mixtures thereof.

25. The method according to claim 17, wherein said culturing step is performed under a condition that a gaseous phase concentration of the organic compound is 50 to 10000 ppm.

26. The method according to claim 17 or 18, wherein said culturing step is performed using a solid culture medium under a condition that a gaseous phase concentration of the organic compound is 50 to 10000 ppm.

27. The method according to claim 17, wherein said culturing step is performed under the conditions of a temperature of 277 to 313K, a pH value of 6.0 to 8.5, and an oxygen concentration which is saturated under the oxygen partial pressure of 0.2 to 21%.

28. The method according to claim 17, wherein said reselecting step is performed under a condition that a gaseous phase concentration of the organic compound is 50 to 10000 ppm.

29. The method according to claim 17, wherein said reselecting step is performed using a liquid culture medium under a condition that a liquid-phase concentration of the organic compound is not less than 500 ppm.

30. The method according to claim 17, wherein said reselecting step is performed under the conditions of a temperature of 277 to 313K, a pH value of 6.0 to 8.5, and an oxygen concentration which is saturated under the oxygen partial pressure of 0.2 to 21%.

* * * * *

UNITED STATES PATENT AND TRADEMARK OFFICE
CERTIFICATE OF CORRECTION

PATENT NO.:    5,919,696

DATED:         July 6, 1999

INVENTOR(S):   Ikeda et al.

It is certified that an error appears in the above-identified patent and that said Letters Patent is hereby corrected as shown below:

Claim 8, column 27, line 15, change "1-bromonapthaline" to --1-bromonaphthalene--.

Signed and Sealed this

Twenty-fifth Day of January, 2000

Attest:

Attesting Officer

Acting Commissioner of Patents and Trademarks